(12) United States Patent
Levin et al.

(10) Patent No.: US 10,751,043 B2
(45) Date of Patent: *Aug. 25, 2020

(54) APPARATUS AND METHOD FOR SUTURING

(71) Applicant: Via Surgical Ltd., Moshav Amirim (IL)

(72) Inventors: Ofek Levin, Moshav Amirim (IL); Arie Levy, Ramat-Gan (IL); Lena Levin, Moshav Amirim (IL)

(73) Assignee: Via Surgical LTD, Moshav Amirim (IL)

( * ) Notice: Subject to any disclaimer, the term of this patent is extended or adjusted under 35 U.S.C. 154(b) by 457 days.

This patent is subject to a terminal disclaimer.

(21) Appl. No.: 15/635,966

(22) Filed: Jun. 28, 2017

(65) Prior Publication Data

US 2017/0296163 A1    Oct. 19, 2017

Related U.S. Application Data

(63) Continuation of application No. 14/362,518, filed as application No. PCT/IB2012/002957 on Dec. 17, 2012, now Pat. No. 9,782,162.

(Continued)

(51) Int. Cl.
 *A61B 17/04* (2006.01)
 *A61B 17/06* (2006.01)
(Continued)

(52) U.S. Cl.
 CPC ...... *A61B 17/0469* (2013.01); *A61B 17/0401* (2013.01); *A61B 17/0483* (2013.01); *A61B 17/0487* (2013.01); *A61B 17/06004* (2013.01); *A61B 2017/00309* (2013.01); *A61B 2017/00323* (2013.01); *A61B 2017/0409* (2013.01); *A61B 2017/0417* (2013.01); *A61B 2017/0472* (2013.01); *A61B 2017/0475* (2013.01);

(Continued)

(58) Field of Classification Search
 None
 See application file for complete search history.

(56) References Cited

U.S. PATENT DOCUMENTS 2,881,762 A    4/1959  Lowrie
3,212,502 A   10/1965  Myers
(Continued)

FOREIGN PATENT DOCUMENTS

CN    101507626 A    8/2009
CN    101969859 A    2/2011
(Continued)

OTHER PUBLICATIONS

Abhishek, et al., 2012, Laparoscopic Umbilical Hernia Repair: Technique Paper, ISRN Minimally Invasive Surgery, pp. 1-4, Article ID 906405.

(Continued)

*Primary Examiner* — Shaun L David

(57) ABSTRACT

The invention generally relates to devices and methods for suturing tissue. The invention provides methods and devices for suturing by pushing two ends of a suture through tissue from a proximal side of the tissue and fastening the two ends together on a distal side of the tissue through one operation of a trigger.

19 Claims, 30 Drawing Sheets

Related U.S. Application Data

(60) Provisional application No. 61/653,792, filed on May 31, 2012, provisional application No. 61/577,038, filed on Dec. 18, 2011.

(51) Int. Cl.
  *A61B 17/00* (2006.01)
  *A61B 17/064* (2006.01)
  *A61B 17/29* (2006.01)

(52) U.S. Cl.
  CPC ........ *A61B 2017/0477* (2013.01); *A61B 2017/0488* (2013.01); *A61B 2017/06042* (2013.01); *A61B 2017/0649* (2013.01); *A61B 2017/06052* (2013.01); *A61B 2017/06176* (2013.01); *A61B 2017/2923* (2013.01)

(56) References Cited

U.S. PATENT DOCUMENTS

| | | |
|---|---|---|
| 3,266,301 A | 8/1966 | Sovatkin |
| 4,069,825 A | 1/1978 | Akiyama |
| 4,235,238 A | 11/1980 | Ogiu et al. |
| 4,391,402 A | 7/1983 | Campbell et al. |
| 4,394,864 A | 7/1983 | Sandhaus |
| 4,458,835 A | 7/1984 | Li et al. |
| 4,536,933 A | 8/1985 | Furutsu |
| 4,809,695 A | 3/1989 | Gwathmey et al. |
| 4,900,303 A | 2/1990 | Lemelson |
| 4,950,285 A | 8/1990 | Wilk |
| 5,037,433 A | 8/1991 | Wilk et al. |
| 5,104,395 A | 4/1992 | Thornton et al. |
| 5,123,913 A | 6/1992 | Wilk et al. |
| 5,174,487 A | 12/1992 | Rothfuss et al. |
| 5,222,961 A | 6/1993 | Nakao et al. |
| 5,242,457 A | 9/1993 | Akopov et al. |
| 5,290,310 A | 3/1994 | Makower et al. |
| 5,330,488 A | 7/1994 | Goldrath |
| 5,356,064 A | 10/1994 | Green et al. |
| 5,359,993 A | 11/1994 | Slater et al. |
| 5,364,002 A | 11/1994 | Green et al. |
| 5,364,022 A | 11/1994 | Ganz |
| 5,392,978 A | 2/1995 | Velez et al. |
| 5,403,346 A | 4/1995 | Loeser |
| 5,425,489 A | 6/1995 | Shichman et al. |
| 5,431,676 A | 7/1995 | Dubrul et al. |
| 5,445,167 A | 8/1995 | Yoon et al. |
| 5,582,616 A | 12/1996 | Bolduc et al. |
| 5,626,587 A | 5/1997 | Bishop et al. |
| 5,662,662 A | 9/1997 | Bishop et al. |
| 5,728,113 A | 3/1998 | Sheds |
| 5,814,058 A | 9/1998 | Carlson et al. |
| 5,827,319 A | 10/1998 | Carlson et al. |
| 5,830,221 A | 11/1998 | Stein et al. |
| 5,895,395 A | 4/1999 | Yeung |
| 5,916,146 A | 6/1999 | Allotta et al. |
| 5,964,394 A | 10/1999 | Robertson |
| 5,968,044 A | 10/1999 | Nicholson et al. |
| 6,156,039 A | 12/2000 | Thal |
| 6,306,149 B1 | 10/2001 | Meade |
| 6,350,269 B1 | 2/2002 | Shipp et al. |
| 6,423,079 B1 | 7/2002 | Blake, III |
| 6,425,900 B1 | 7/2002 | Knodel et al. |
| 6,447,524 B1 | 9/2002 | Knodel et al. |
| 6,494,886 B1 | 12/2002 | Wilk et al. |
| 6,530,933 B1 | 3/2003 | Yeung et al. |
| 6,607,542 B1 | 8/2003 | Wild |
| 6,638,286 B1 | 10/2003 | Burbank et al. |
| 6,733,506 B1 | 5/2004 | McDevitt et al. |
| 7,004,970 B2 | 2/2006 | Cauthen, III et al. |
| 7,125,413 B2 | 10/2006 | Grigoryants et al. |
| 7,141,057 B2 | 11/2006 | Burbank et al. |
| 7,338,502 B2 | 3/2008 | Rosenblatt |
| 7,398,908 B2 | 7/2008 | Holsten et al. |
| 7,431,730 B2 | 10/2008 | Viola |
| 7,591,783 B2 | 9/2009 | Boulais et al. |
| 7,594,923 B2 | 9/2009 | Fallin et al. |
| 7,625,386 B2 | 12/2009 | Abe et al. |
| 7,658,311 B2 | 2/2010 | Boudreaux |
| 7,704,261 B2 | 4/2010 | Sakamoto et al. |
| 7,708,180 B2 | 5/2010 | Murray et al. |
| 7,776,066 B2 | 8/2010 | Onuki et al. |
| 7,842,047 B2 | 11/2010 | Modesitt et al. |
| 7,850,701 B2 | 12/2010 | Modesitt et al. |
| 7,913,891 B2 | 3/2011 | Doll et al. |
| 7,918,377 B2 | 4/2011 | Measamer et al. |
| 7,918,868 B2 | 4/2011 | Marshall et al. |
| 7,959,640 B2 | 6/2011 | Kantsevoy et al. |
| 7,967,831 B2 | 6/2011 | Rosenberg et al. |
| 8,034,076 B2 | 10/2011 | Criscuolo et al. |
| 8,038,686 B2 | 10/2011 | Huitema et al. |
| 8,070,035 B2 | 12/2011 | Holsten et al. |
| 8,075,572 B2 | 12/2011 | Stefanchik et al. |
| 8,091,756 B2 | 1/2012 | Viola |
| 8,114,099 B2 | 2/2012 | Shipp |
| 8,132,705 B2 | 3/2012 | Viola et al. |
| 8,157,146 B2 | 4/2012 | Edoga et al. |
| 8,177,795 B2 | 5/2012 | Niese et al. |
| 8,211,126 B2 | 7/2012 | Yeh et al. |
| 8,216,272 B2 | 7/2012 | Shipp |
| 8,277,373 B2 | 10/2012 | Maahs et al. |
| 8,282,670 B2 | 10/2012 | Shipp |
| 8,343,176 B2 | 1/2013 | Criscuolo et al. |
| 8,535,339 B2 | 9/2013 | Levin et al. |
| 8,603,118 B2 | 12/2013 | Yeh et al. |
| 8,733,616 B2 | 5/2014 | Badly et al. |
| 8,814,885 B2 | 8/2014 | Domingo |
| 8,961,530 B2 | 2/2015 | Bhatnagar et al. |
| 9,724,088 B2 | 8/2017 | Domingo |
| 9,770,262 B2 | 9/2017 | Clancy et al. |
| 9,782,162 B2 | 10/2017 | Levin et al. |
| 9,872,727 B2 | 1/2018 | Motai |
| 2001/0039436 A1* | 11/2001 | Frazier ............ A61B 17/00234 606/219 |
| 2001/0046646 A1 | 11/2001 | Koba |
| 2002/0068951 A1 | 6/2002 | Burbank et al. |
| 2002/0107530 A1 | 8/2002 | Sauer et al. |
| 2003/0139752 A1 | 7/2003 | Pasricha et al. |
| 2003/0208209 A1 | 11/2003 | Gambale et al. |
| 2004/0098045 A1 | 5/2004 | Grafton et al. |
| 2004/0138681 A1 | 7/2004 | Pier |
| 2004/0204723 A1 | 10/2004 | Kayan |
| 2005/0131390 A1 | 6/2005 | Heinrich et al. |
| 2006/0235443 A1 | 10/2006 | Huitema et al. |
| 2007/0045379 A1 | 3/2007 | Shelton |
| 2007/0112361 A1 | 5/2007 | Schonholz et al. |
| 2007/0179509 A1 | 8/2007 | Nagata et al. |
| 2007/0250064 A1 | 10/2007 | Darois et al. |
| 2007/0270637 A1 | 11/2007 | Takemoto et al. |
| 2008/0091219 A1 | 4/2008 | Marshall et al. |
| 2008/0097523 A1 | 4/2008 | Bolduc et al. |
| 2008/0110958 A1 | 5/2008 | McKenna et al. |
| 2008/0255591 A1 | 10/2008 | Harada et al. |
| 2008/0314954 A1 | 12/2008 | Boudreaux |
| 2009/0018554 A1 | 1/2009 | Thorne et al. |
| 2009/0114233 A1 | 5/2009 | Edoga et al. |
| 2009/0206144 A1 | 8/2009 | Doll et al. |
| 2009/0209980 A1 | 8/2009 | Harris |
| 2009/0222083 A1 | 9/2009 | Nguyen et al. |
| 2009/0259251 A1 | 10/2009 | Cohen |
| 2010/0016870 A1 | 1/2010 | Campbell |
| 2010/0069930 A1 | 3/2010 | Roslin et al. |
| 2010/0094248 A1 | 4/2010 | Nguyen et al. |
| 2010/0096435 A1 | 4/2010 | Fuchs et al. |
| 2010/0145361 A1 | 6/2010 | Francischelli et al. |
| 2010/0160931 A1 | 6/2010 | Karpiel et al. |
| 2010/0191283 A1 | 7/2010 | Foerster et al. |
| 2010/0292710 A1 | 11/2010 | Daniel et al. |
| 2010/0298774 A1 | 11/2010 | Igov |
| 2010/0318107 A1 | 12/2010 | Mizrahy et al. |
| 2010/0327042 A1 | 12/2010 | Amid et al. |
| 2010/0331863 A2 | 12/2010 | Saliman et al. |
| 2011/0071548 A1 | 3/2011 | Yeh et al. |
| 2011/0092992 A1 | 4/2011 | Darois et al. |

(56) References Cited

U.S. PATENT DOCUMENTS

| | | |
|---|---|---|
| 2011/0098728 A1 | 4/2011 | McDevitt et al. |
| 2011/0118757 A1 | 5/2011 | Pierce |
| 2011/0130774 A1 | 6/2011 | Criscuolo et al. |
| 2011/0178534 A1 | 7/2011 | Whitman et al. |
| 2011/0319932 A1 | 12/2011 | Avelar et al. |
| 2012/0016389 A1 | 1/2012 | Kantsevoy et al. |
| 2012/0089157 A1 | 4/2012 | Forsell |
| 2012/0097731 A1 | 4/2012 | Knodel et al. |
| 2012/0109132 A1 | 5/2012 | Ellis et al. |
| 2012/0116424 A1 | 5/2012 | Lee et al. |
| 2012/0191091 A1 | 7/2012 | Allen |
| 2012/0193394 A1 | 8/2012 | Holcomb et al. |
| 2012/0232586 A1 | 9/2012 | Yeh et al. |
| 2012/0245629 A1 | 9/2012 | Gross et al. |
| 2012/0248171 A1 | 10/2012 | Bailly et al. |
| 2012/0265218 A1 | 10/2012 | Chen et al. |
| 2012/0310259 A1 | 12/2012 | Sorrentino et al. |
| 2012/0330354 A1 | 12/2012 | Kane et al. |
| 2012/0330356 A1 | 12/2012 | Rosenberg |
| 2013/0012961 A1 | 1/2013 | Reeser |
| 2013/0018394 A1 | 1/2013 | Gambale |
| 2013/0186936 A1 | 7/2013 | Shelton, IV |
| 2013/0317524 A1 | 11/2013 | Grigoryants et al. |
| 2014/0058417 A1 | 2/2014 | Levy et al. |
| 2014/0257339 A1 | 9/2014 | Levy et al. |
| 2015/0272566 A1 | 10/2015 | Arai et al. |
| 2015/0351862 A1 | 12/2015 | Clancy et al. |
| 2015/0360019 A1 | 12/2015 | Clancy et al. |
| 2016/0310146 A1 | 10/2016 | Levy et al. |
| 2017/0265858 A1 | 9/2017 | Rosenberg |

FOREIGN PATENT DOCUMENTS

| | | |
|---|---|---|
| EP | 1 206 924 A1 | 5/2002 |
| EP | 1 721 575 A2 | 11/2006 |
| EP | 1 759 812 A1 | 3/2007 |
| JP | 5-161655 A | 6/1993 |
| WO | 1996/03925 A1 | 2/1996 |
| WO | 2001/65997 A2 | 9/2001 |
| WO | 2007/139785 A2 | 12/2007 |
| WO | 2009/100242 A2 | 8/2009 |
| WO | 2010/084424 A1 | 7/2010 |
| WO | 2011/068533 A1 | 6/2011 |

OTHER PUBLICATIONS

Extended European search report dated Apr. 22, 2015, for European patent application 12859826.5, which application is a regional stage entry of International Patent Application PCT/IB2012/002957, filed Dec. 17, 2012 (5 pages).

Gillian, et al., 2002, Laparoscopic Incisional and Ventral Hernia Repair (LIVH): An Evolving Outpatient Technique, JSLS 6(4):315-322.

International Search Report and Written Opinion dated Jun. 20, 2013 in related international application PCT/IB12/02957, filed Dec. 17, 2012 (10 pages).

International Search Report and Written Opinion dated Feb. 13, 2015, for International Patent Application No. PCT/US2014/001572, filed Mar. 6, 2014 (18 pages).

International Search Report and Written Opinion dated Oct. 29, 2013, for International Patent Application No. PCT/IB2013/000647, filed Feb. 15, 2013 (17 pages).

International Search Report and Written Opinion dated Sep. 26, 2016, for International Patent Application PCT/IB16/00571 with International filing date Apr. 19, 2016 (7 pages).

Nguyen, et al., 2008, Postoperative Pain After Laparoscopic Ventral Hernia Repair: a Prospective Comparison of Clips Versus Tacks, JSLS 12:113-116.

Notification Concerning Transmittal of International Preliminary Report on Patentability for Application No. PCT/IB2014/001572 dated Sep. 24, 2015.

Web page <http://www.covidien.com/silsstitch/pages.aspx> accessed on Mar. 29, 2012 (2 pages).

Web page <http://www.lsisolutions.com/rd180deviceanatomy> accessed on Mar. 29, 2012 (1 page).

* cited by examiner

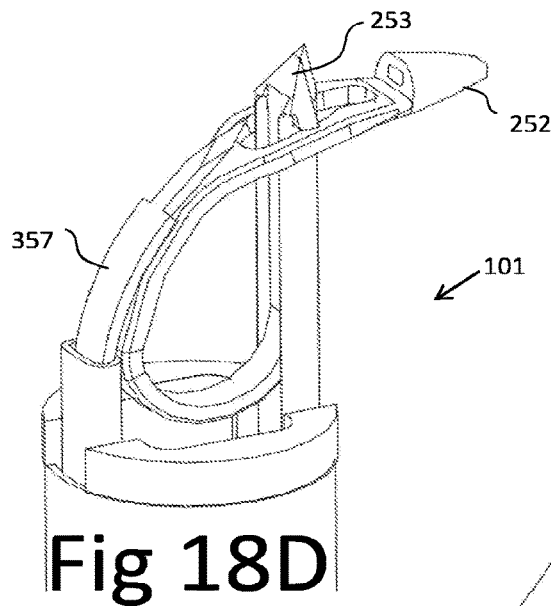
Fig 18D
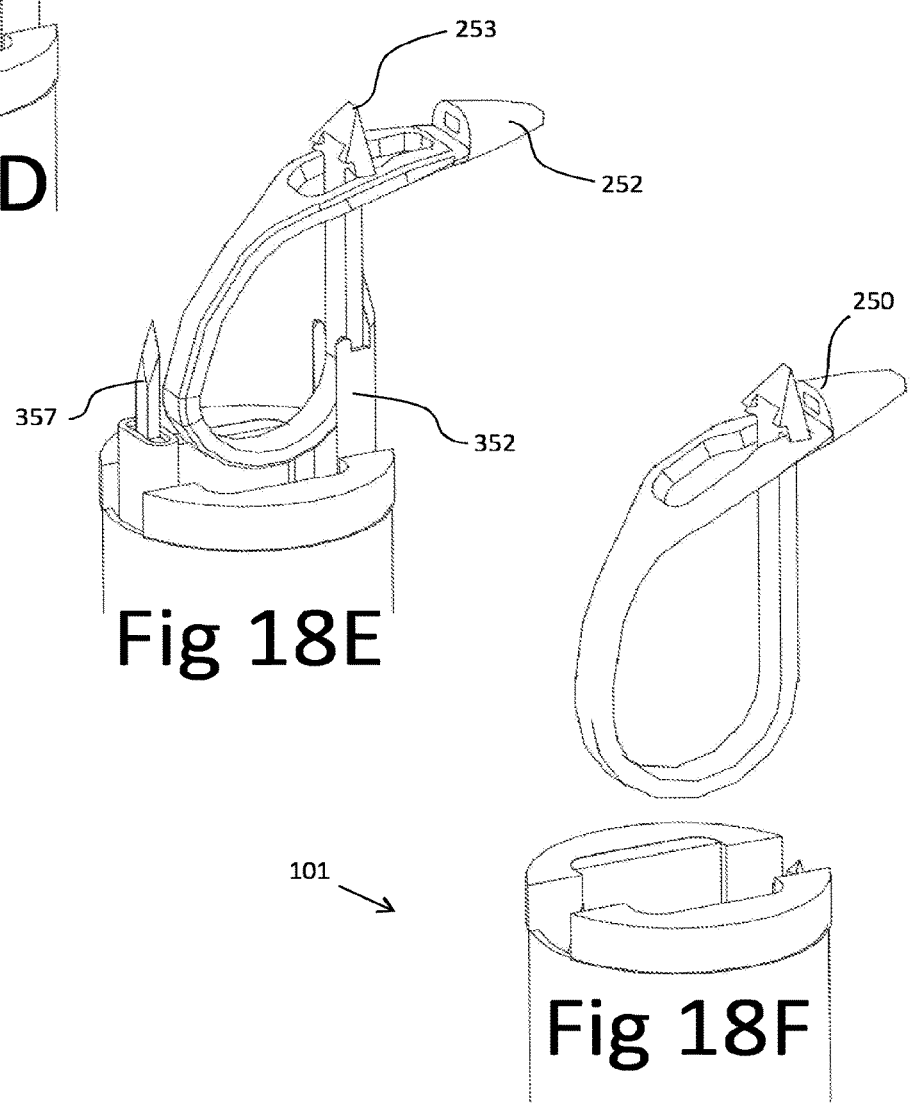
Fig 18E
Fig 18F

APPARATUS AND METHOD FOR SUTURING

CROSS-REFERENCE TO RELATED APPLICATIONS

This application is a continuation of U.S. patent application Ser. No. 14/362,518, filed Jun. 3, 2014, which application issued as U.S. Pat. No. 9,782,162 B2 on Oct. 10, 2017, and is a national stage entry of PCT/IB2012/002957 with an International Filing Date of Dec. 17, 2012, which application claims priority to U.S. Provisional Application No. 61/577,038, filed on Dec. 18, 2011, and to U.S. Provisional Application No. 61/653,792 filed on May 31, 2012, the contents of each of which are hereby incorporated by reference in their entirety.

FIELD OF THE INVENTION

The invention generally relates to sutures, delivery devices, and methods of use thereof.

BACKGROUND

Suturing is a common operation for closing surgical incisions. Suturing is also used to affix prostheses to target sites. However, suturing can present particular difficulties in laparoscopic and endoscopic surgery because those procedures take place entirety within a patient's body.

Some common devices deliver a suture to tissue within the body and fasten it by pushing one end of the suture through tissue and then pulling the same end back through the tissue. This leaves two ends of the suture on the side closest to the physician, who then ties the two ends together. Other devices are designed to deliver a suture that is structured to be cinched closed without tying a knot, but such sutures require time-consuming and difficult manipulation with endoscopic forceps or similar tools.

Since existing devices for laparoscopic suturing typically require difficult, time-consuming manipulation of the suture with forceps or other instruments, the incision must be kept open for a prolonged amount of time, which increases the risk of infection or other surgical complications. Further, tying these sutures closed requires difficult manipulation of small instruments, thus require a significant degree of expertise in operation

SUMMARY

The invention provides a mechanical self-locking suture and accompanying delivery device. The delivery device and suture of the invention are configured to deliver an open suture to a target tissue and then to automatically close the suture upon deployment from the device. The suture is designed to become locked upon deployment from the delivery device into the target tissue. Delivery devices and sutures of the invention allow for rapid delivery of sutures to target tissue, while eliminating difficulties associated with manipulating small structures within the body during the suturing process. The delivery device and suture of the invention are particularly useful for minimally-invasive surgery (e.g. laparoscopic surgery) in which the ability of the surgeon visualize the tissue and to manipulate the suture is limited.

In certain aspects, sutures of the invention include a flexible body having a first member disposed at one end and a second member disposed at the other. The two members define a fastening structure. For example, the first member can be a hook and the second member can be a loop.

Passage of the hook through the loop fastens the suture into a closed loop. The hook and the loop are generally disposed at the ends of the suture body, such that the body can include a substantially smooth cross-sectional shape along its length (e.g., along about half or more of the entire length of the suture). The suture is generally designed to be pushed through tissue at either or both of its ends. Either or both ends can include, for example, a beveled tip or tapered portion to facilitate insertion through tissue. In certain embodiments, the hook is tapered from a proximal to a distal end.

Further, either or both end can include a structure designed to co-operate with a delivery device such as, for example, protrusions or indentations configured to mate with an insertion device. As the suture can be designed to be pushed through tissue at both ends while having a U shape, the push-able surfaces can each face inward towards a center of the body member. In some embodiments, one or more of the protrusions or indentations are provided at distal ends of the suture. Insertion and delivery can be accomplished through the use of insertion needles provided by a delivery device or manipulated by a practitioner.

In some embodiments, a suture of the invention requires no moving parts and can be integrally formed of a single piece of material, allowing for affordable and easy manufacturing. Any suitable material can be used such as, for example, a metal, a monofilament, a multifilament, a biodegradable material, a polymer, nylon, PDS, PGLA, PLA, a non-degradable material, polypropylene, polyethylene, or a nickel-titanium alloy.

The end members of the suture act to fasten the suture. For example, in hook-and-loop embodiments, passage of the hook portion of the suture through the loop portion can fasten the suture closed in part because the loop can be dimensioned such that it is not substantially larger than the hook member. The hook member can include barbs or wings (e.g., fin-like structures) that do not freely pass through the opening of the loop. In some embodiments, either the fins or the loop must deform somewhat for the hook to pass through the loop.

Pushing the hook through the loop fastens the suture in a secure, closed loop due to the action of the barb or fin structures on the hook and/or due to the dimensions of the loop. Further, the loop can feature a "keyhole" shape having, for example, a portion of diminished width near the end such that tension on the suture causes the hook end of the body to be secured into the narrow end of the keyhole loop, thus locking the suture in its closed conformation. In some embodiments, the second member includes an aperture with a wide section and a narrow section, the narrow section being distal to the wide section and having a width such that the narrow section retains the first member. The second member can further have a protrusion located distal to the aperture.

In other aspects, delivery devices of the invention include a shaft that has a delivery mechanism at least partially disposed therein. The delivery mechanism is configured to releasably engage a suture at least partially disposed within the shaft in an open configuration, deliver the suture from the shaft to a target tissue, form the suture into a closed configuration beneath a surface of the target tissue, and release from the closed suture.

In some embodiments, the device includes a trigger on a handle. Operation of the trigger causes a first end of a body member of the suture to move towards a second end of the body, fastening the two ends together. In certain embodiments, both ends of the suture are inserted into tissue from a side of the tissue proximal to the operator and the suture is closed and fastened on a side of the tissue distal from the operator.

The shaft carries a suture (or a cartridge loaded with sutures) to a target site in a tissue. Operation of the trigger fastens a suture in place in a closed loop while releasing it from the delivery tip.

The delivery mechanism can operate via a needle member that pushes the suture in a direction away from a handle of the device. The mechanism may further include two (or more) push rods, each of which provides a needle member at an end of the delivery mechanism distal to the handle. Each needle member couples with a portion of the suture for delivery. Delivery and fastening can be accomplished by the operation of one or more of a delivery needle disposed within the shaft that pushes the suture towards and into the tissue. For example, a needle member of the delivery mechanism can push the suture away from the handle, towards the target. Fastening is accomplished through the action of the delivery mechanism. In some embodiments, delivery and fastening involves two push rods in the delivery mechanism. The push rods can extend from the handle to the delivery tip. Each push rod terminates with an insertion needle that couples with (e.g., holds and/or pushes) a portion of the suture. Operation of the trigger causes each push rod to translate relative to the shaft and relative to the other push rod. Cooperative insertion and delivery is accomplished via push rods that drive the ends of the suture through the tissue. Upon activation of the trigger, one push rod extends from the delivery tip, following a curved path so that one end of the suture meets the other end on a side of the tissue distal to the delivery device. The push rods translate relative to each other and to the shaft to coordinate the suturing. A predetermined sequence of relative translations of the two push rods can be coordinated by a linkage between each push rod and a slot wheel mechanism in the handle of the device having an irregular slot. The push rods extend along a length of the shaft from the handle to the delivery tip.

In certain embodiments, a single operation of the trigger causes a loop end of a suture to be pushed through the tissue while a hook end of the suture is also pushed through the tissue from the same side (e.g., the proximal side, with reference to the operator holding the handle) and brought into contact with the loop end on the distal side of the tissue. The hook member can be guided towards the loop member through the action of a shape memory material in the insertion needles.

The independent and coordinated translation of the push rods and insertion needles is governed by a linkage to a set of slot wheels associated with the handle. The trigger can include a squeezable handle that interacts with gears to cause rotation of the slot wheel set. The device can also include an articulation joint to bend the shaft.

In some embodiments, the delivery tip is configured to receive a cartridge loaded with a plurality of sutures. Cartridges can be loaded with sutures of different sizes, thus allowing the device to be used to deliver sutures of different sizes by swapping out cartridges. A single cartridge form-factor may be loaded with sutures of varying sizes, e.g., through the use of a spacer.

Another aspect of the invention provides a cartridge that holds sutures and can be loaded into a delivery device. The cartridges structure cooperates with the mechanical structure of the device so that the device can deliver and fasten sutures within a patient's body. The cartridge is able to accommodate sutures of different sizes.

In some embodiments, the cartridge can use a spacer that is adapted to allow for delivery of different sizes of sutures using the same applicator device and the same sequence of needle movements. The spacer can be interchangeable within the cartridge, the cartridge can be interchangeable within the device, or both. Within a cartridge, the size of the spacer is set according to the size of the sutures within the cartridge. A small spacer can be provided to accommodate long sutures while a large spacer accommodates short sutures.

In some embodiments, the cartridge has a release slot. The release slot is designed to exert some resistance, or friction, on the suture. The resistance pulls a suture that is not fastened out of tissue during retraction of the suture delivery device, to provide a fail-safe mechanism for retrieving un-fastened sutures. Further, the resistance maintains operable contact between the suture and the suture delivery device during delivery.

In certain embodiments, the cartridge can be inserted into an end of an shaft of the suture delivery device.

Other aspects of the invention provide a method for suturing tissue by delivering to a wound at least one suture. At least one of the delivered sutures includes a flexible body having two ends, a first member disposed at a first end of the body, and a second member disposed at a second end of the body. Delivery according to the methods of the invention causes the first end of the body to mate with and be retained by the second end of the body, thereby forming the suture into a closed configuration.

Because the suture can be delivered by a device with an elongated shaft, the wound can be inside of a body (e.g., spaced away from the handle and operator by a distance).

The first and second members generally define a fastening structure. In some embodiments the first member is a hook (optionally tapered from a proximal to a distal end). The second member can present a loop-structure, e.g., an aperture. The aperture can further include a wide section and a narrow section, the narrow section being distal to the wide section and having a width such that the narrow section retains the first member.

Either or both of the first and second members may further include a structure such as a protrusion or indention to mate with a delivery device. Either protrusion may be located at an end of a suture (e.g., at distal ends of the first or second member). The suture can include any suitable material such as, for example, metal, a monofilament, a multifilament, a biodegradable material, a polymer, nylon, PDS, PGLA, PLA, a non-degradable material, polypropylene, polyethylene, and a nickel-titanium alloy.

In certain aspects, the invention provides a method for suturing tissue by delivering to a wound at least one suture using a suturing device that includes an shaft configured to releasably carry the suture in an open configuration and a delivery mechanism that forms the suture into the closed configuration and releases it from the shaft.

Methods can include pushing the suture in a direction away from the operator with a push rod or inserting at least a first end of the suture through an aperture in a second end of the suture. One or more needle members can be provided by one or more push rods. Where two push rods each provide a needle member, the needle members can couple with portions of the suture.

In some embodiments, the method includes pushing two ends of the suture through tissue from a proximal side of the tissue and fastening the two ends together on a distal side of the tissue. This can be accomplished through one single operation of a trigger. The suture is pushed into place at the surgical site by a mechanism of the delivery device coupled to the trigger. Methods further include delivering a suture at an angle away from the shaft by articulating the shaft via an articulation joint. Suture sizes can be changed by changing a cartridge of sutures in the device.

Another aspect of the invention provides a method for securing a medical prosthesis to tissue. Securing the prosthesis is accomplished through delivering a suture to a target tissue that has a prosthesis applied to it. The suture includes a flexible body having two ends, a first member disposed at a first end of the body, and a second member disposed at a second end of the body. Delivery according to the methods of the invention causes the first end of the body to mate with and be retained by the second end of the body, thereby forming the suture into a closed configuration and securing the prosthesis to the tissue. The prosthesis can be a mesh, such as a hernia mesh. Because the suture can be delivered by a device with an elongated shaft, the target tissue can be inside of a body.

The prosthesis can be secured by employing a fastening structure provided by the first and second members. In some embodiments the first member is a hook (optionally tapered from a proximal to a distal end). The second member can present a loop-structure, e.g., an aperture. The aperture can further include a wide section and a narrow section, the narrow section being distal to the wide section and having a width such that the narrow section retains the first member.

Suturing the prosthesis may be facilitated by a structure such as an indentation or protrusion on the first member, the second member, or both. Such a structure can be provided to mate with a delivery device. Either protrusion may be located at an end of a suture (e.g., at distal ends of the first or second member). The suture can include any suitable material such as, for example, a metal, a monofilament material, a multifilament material, a biodegradable material, a polymer, nylon, PDS, PGLA, PLA, a non-degradable material, polypropylene, polyethylene, and a nickel-titanium alloy. In some embodiments, methods include suturing the prosthesis with an integrally formed suture.

Methods of the invention include securing the prosthesis with a suture of a selected size. In some embodiments, this is by using an interchangeable cartridge from a set in which the cartridges include sutures of differing sizes. The delivery tip of the shaft can be configured to house a suture cartridge that is pre-loaded with sutures. Suture cartridges can be pre-loaded with sutures of different sizes and then interchangeably loaded into the delivery device. By these means, a single suturing device can deliver sutures of different sizes. Each suture is delivered via a simple single trigger-pull procedure.

BRIEF DESCRIPTION OF THE DRAWINGS

FIGS. 18A-18F depict the operation of a suture applicator of certain embodiments.

DETAILED DESCRIPTION

The current invention provides sutures, delivery devices, and methods for fastening a suture to tissue. The invention provides methods and devices for suturing by pushing two ends of a suture through tissue from a proximal side of the tissue and fastening the two ends together on a distal side of the tissue through one operation of a trigger. Sutures and devices of the invention are useful for securing a prosthetic device to a tissue or for wound closure or any other medical need requiring the use of a suture.

Figure 1A:
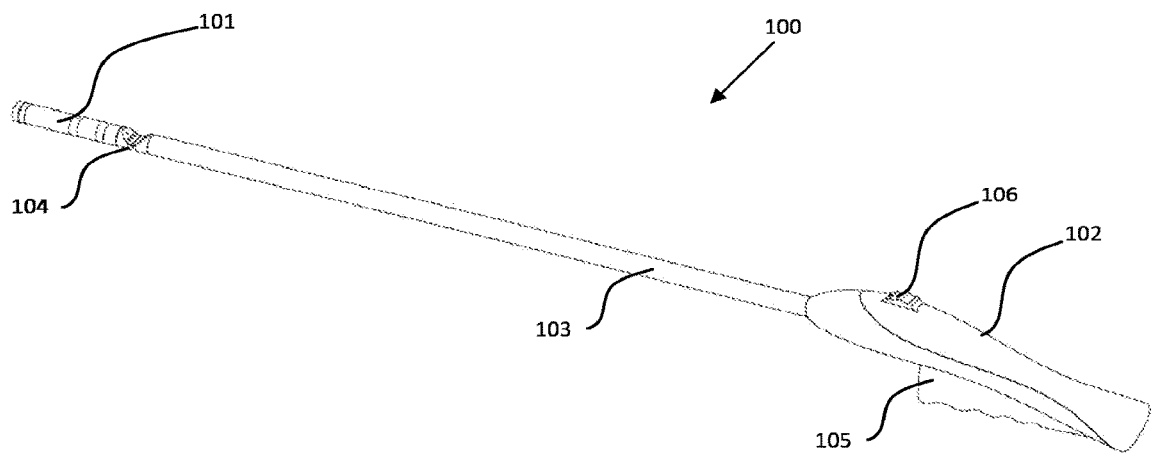
FIGS. 1A and 1B illustrate one embodiment of a suture applicator.
Figure 1B:
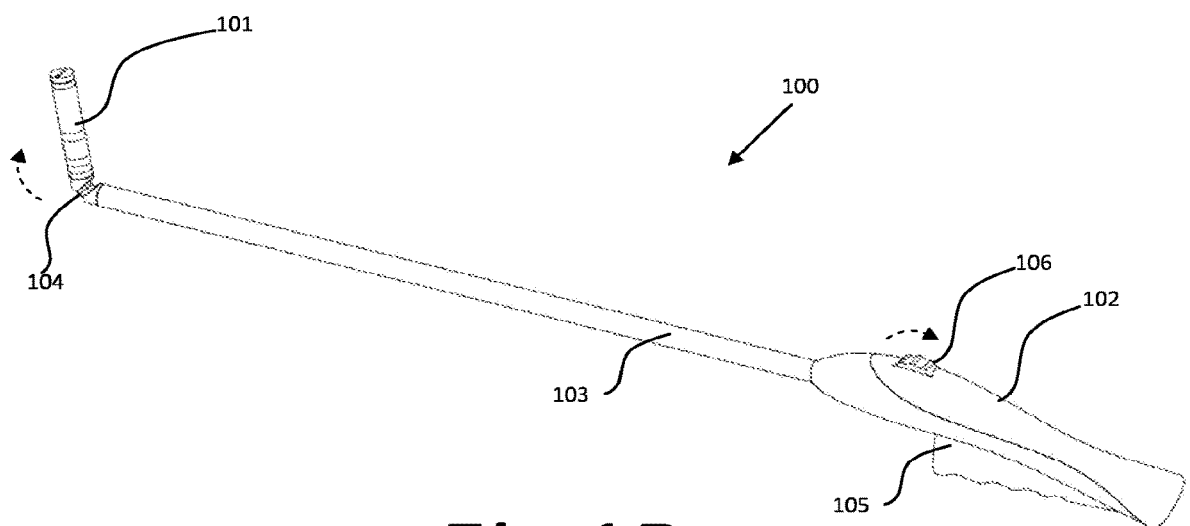

FIGS. 1A and 1B depict a suture applicator 100 according to certain embodiments. Suture applicator 100 is adapted to place and secure at least one suture inside a tissue during a minimal invasive surgical operation. Suture applicator 100 has an applicator section 101 and a handle section 102 connected via shaft 103. Applicator section 101 is adapted to pass through an incision or standard trocar, and to make contact with, and insert a suture into, the tissue.

Handle section 102 allows a practitioner to control suture application. Handle section 102 includes trigger 105, which may generally include a lever mechanism. Operation of trigger 105 delivers and fastens a suture as described below.

In certain embodiments, shaft 103 is articulated around an articulation joint 104 in order to place a suture inside the tissue in a correct angle in respect to the tissue surface (FIG. 1B). Handle 102 includes articulation knob 106 adapted to control the articulation.

Figure 2A:
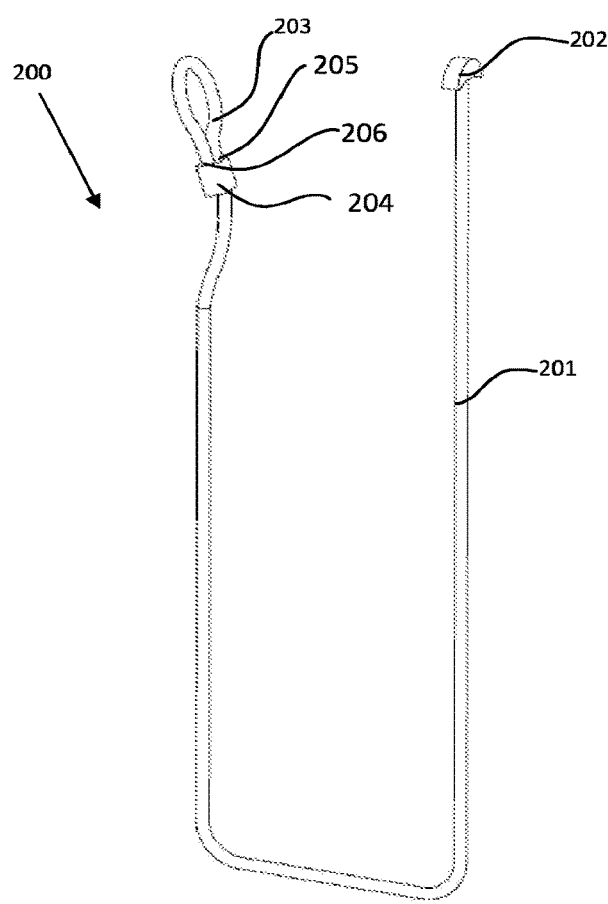
FIGS. 2A and 2B illustrate a suture applied by the suture applicator.
Figure 2B:
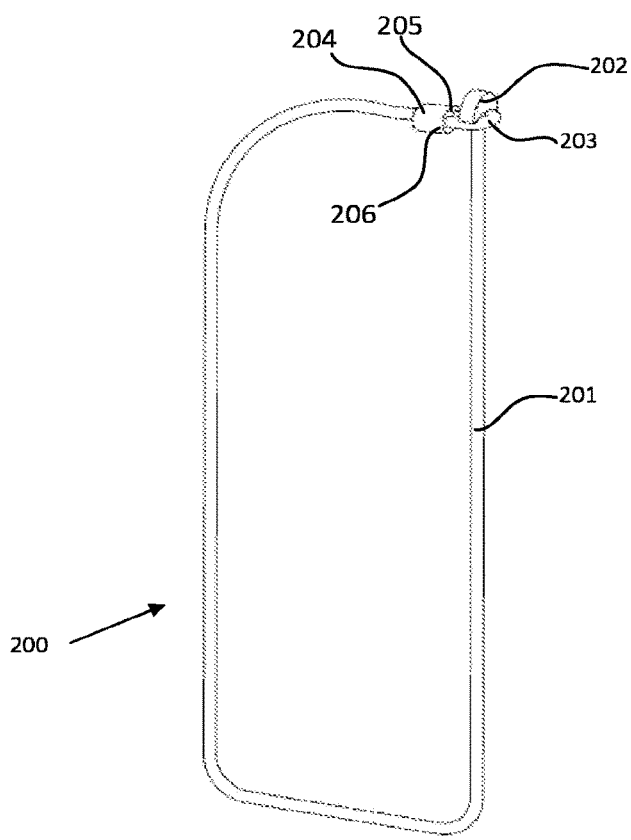

FIGS. 2A and 2B illustrate a suture 200 according to certain embodiments. Suture 200 includes wire 201. A hook 202 is connected to one end of wire 201 and a loop 202 is connected to the other end. Suture 200 can include monofilament, multifilament or metallic material, in addition it can be made from a biodegradable material.

Suture 200 is characterized by at least two configurations: an open configuration (FIG. 2A), in which hook 202 and loop 203 are not connected to each other therefore allowing the insertion of suture 200 into tissue; and a closed configuration (FIG. 2B) in which hook 202 is inserted through loop 203 therefore forming a closed loop and securing suture 200 to the tissue.

In certain embodiments, loop 203 has a diameter that can be decreased such that loop 203 is tightened (e.g., once hook 202 is inserted through loop 203), thus preventing unintended disengagement of hook 202 from loop 203. Tightening is accomplished by loop holder 204. Loop holder 204 includes two holes 205 and 206. Wire 201 extends through hole 205 and hole 206. The wire 201 is connected to said loop holder 204 at hole 206 (by welding gluing or any other attachment mean) while free movement of wire 201 in relation the loop holder 204 at hole 205 is allowed. Thus, once tension is applied to wire 201, loop 203 is tightened.

Additionally or alternatively, hook 202 can be expanded once it is inserted through loop 203 (e.g., while loop 203 remains static). Expansion can be provided by shaping hook 202 as an arrowhead which deforms and compresses to pass through loop 203 and then expands back to its original shape.

Figure 3A:
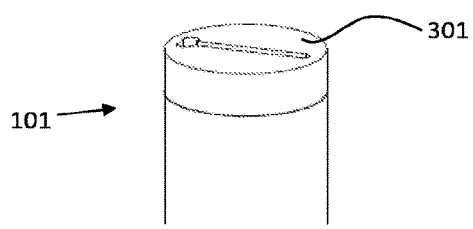
FIGS. 3A-3G illustrate various stages during application of a suture.
Figure 3B:
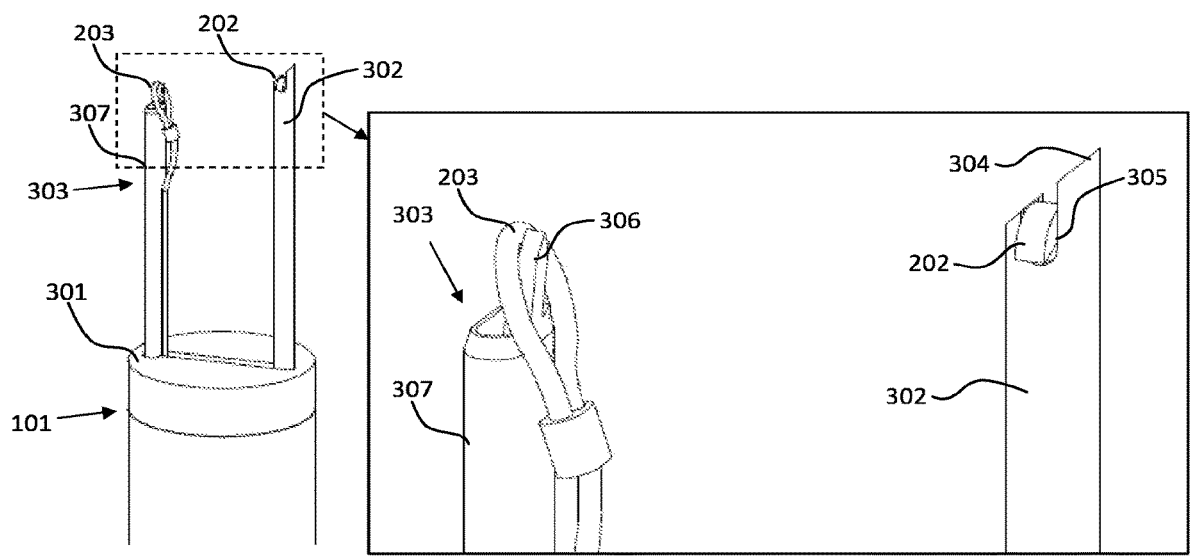

FIGS. 3A-3G illustrate a method of delivering and fastening suture 200 into tissue 300 (not shown). At the first stage (FIG. 3A), distal tip 301 of suture applicator 100 is brought to the tissue surface. Next, suture 200 is inserted into the tissue by hook insertion needle 302 and loop insertion needle 303 (FIG. 3B).

Hook insertion needle 302 is adapted to insert hook 202 of suture 200 into tissue 300. In some embodiments, hook insertion needle 302 is characterized by an open cross section (e.g. "C" shaped) such that hook insertion needle 302 could be removed from suture 200 once the suture is closed. Hook insertion needle 302 is characterized by a sharp distal tip 304 adapted to penetrate through tissue 300. Distal tip 304 of hook insertion needle 302 includes two of lateral groove 305 to hold hook 202 during said insertion.

Loop insertion needle 303 is adapted to insert loop 203 into tissue 300 in curved path such that loop 203 is positioned directly above hook 202. Loop insertion needle 303 has a flexible needle 306 housed inside an insertion tube 307. Flexible needle 306 is characterized by a sharp and narrow tip adapted to penetrate the tissue while holding loop 203. The distal section of flexible needle 306 is pre-curved (see FIG. 3C). During initial insertion, flexible needle 306 is held straight inside said insertion tube 307. In certain embodiments, flexible needle 306 includes a super-elastic material such as, for example, Nitinol.

Figure 3C:
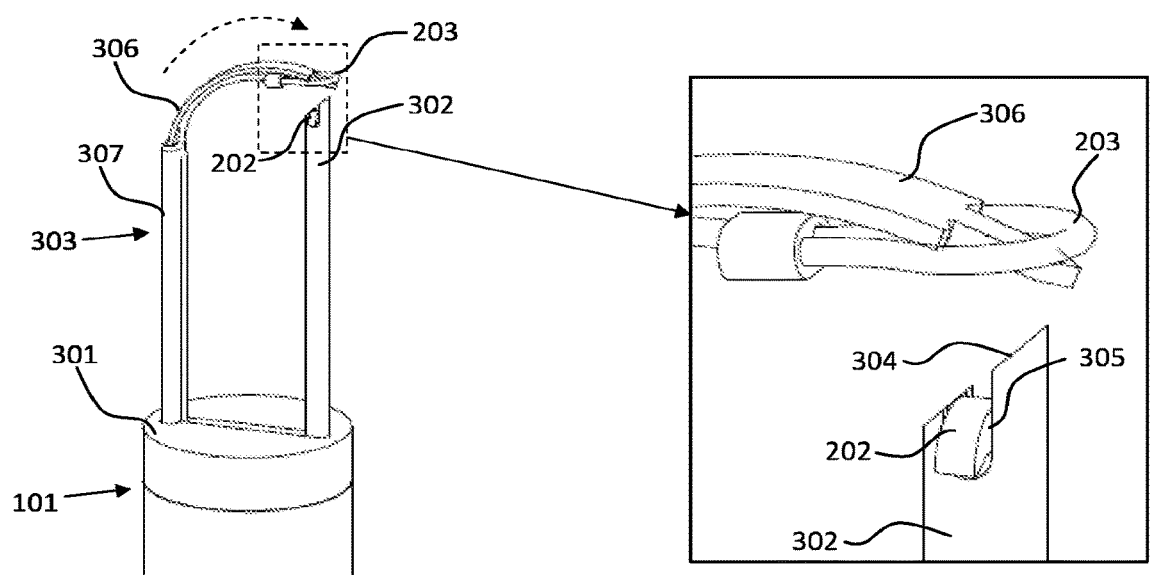
Figure 3D:
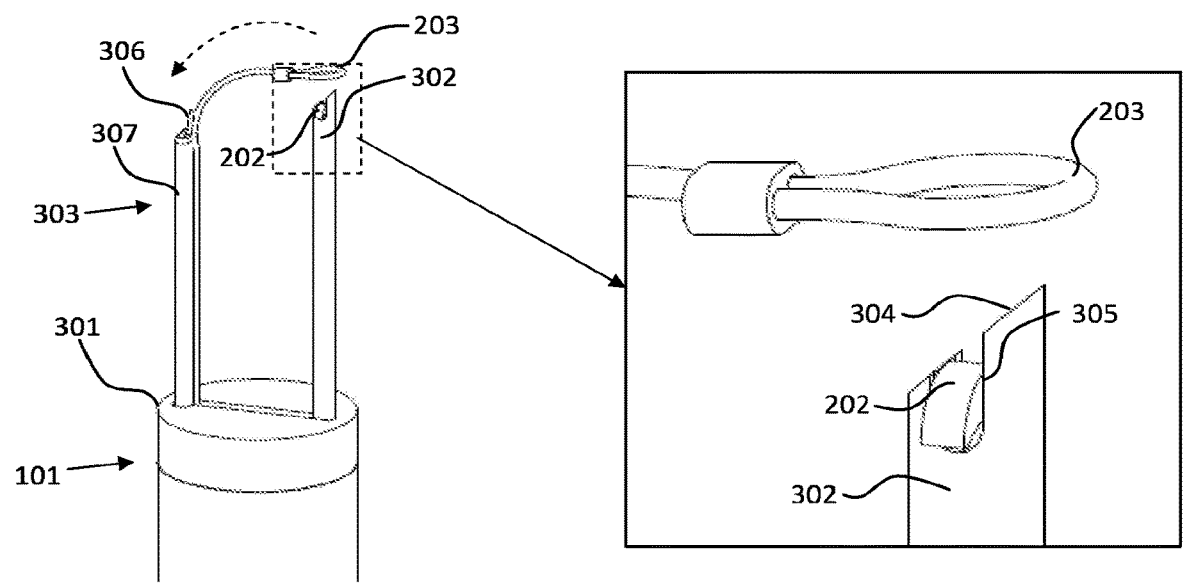
Figure 3E:
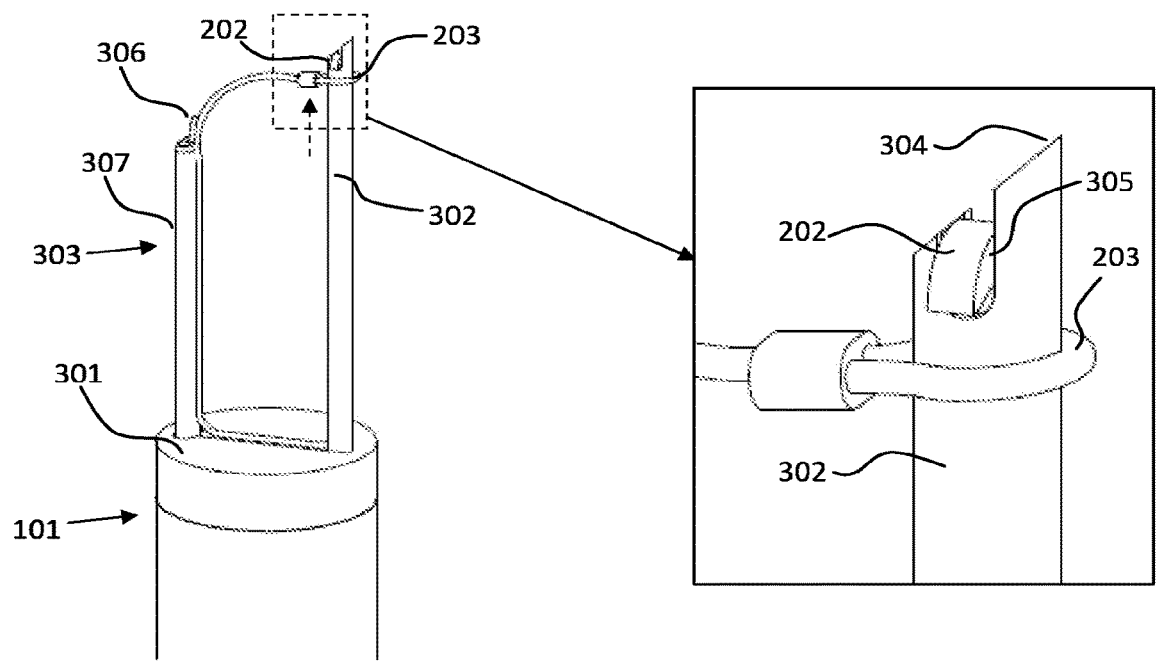
Figure 3F:
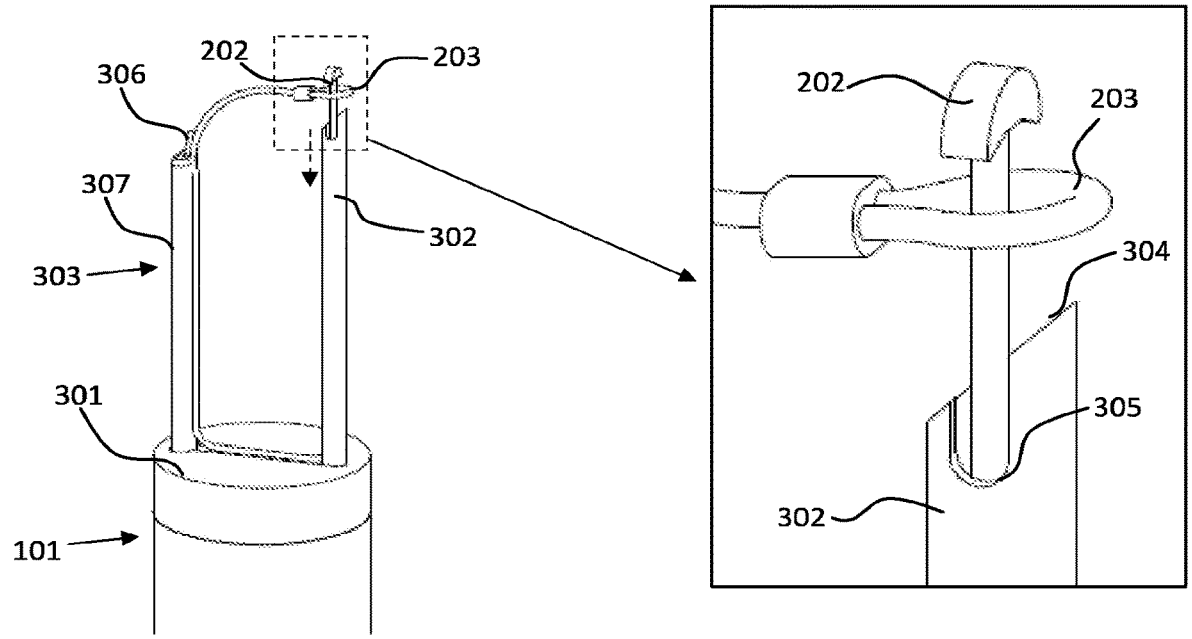
Figure 3G:
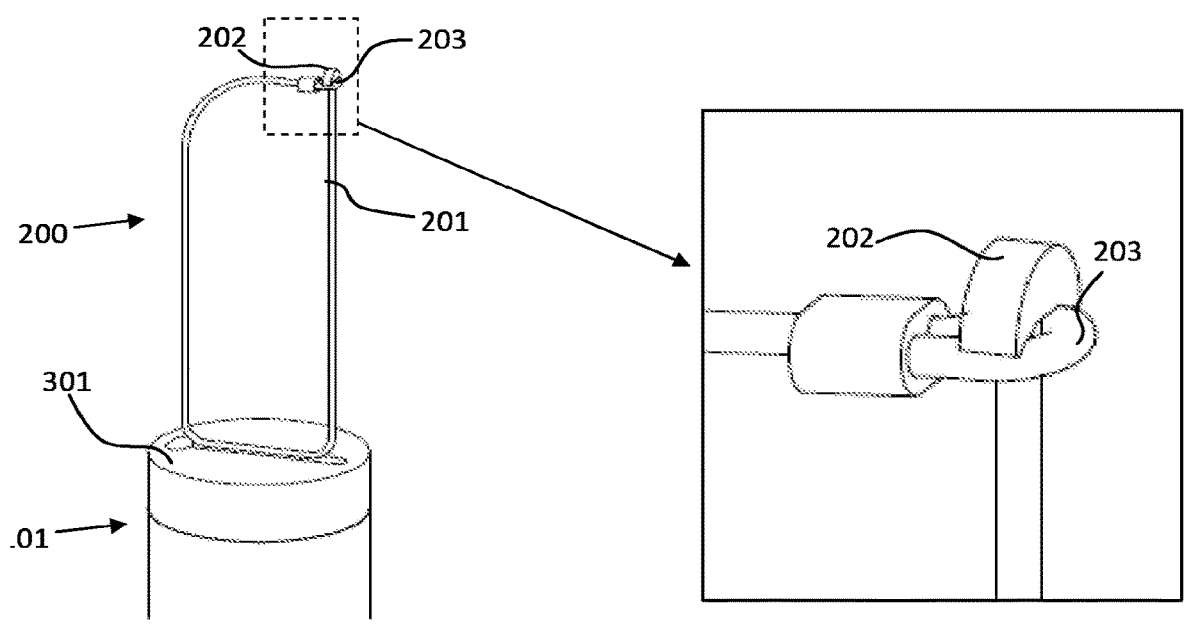

As shown in FIG. 3C, flexible needle 306 is extended out of said insertion tube 307, penetrating tissue 300 in a curved path while pulling and positioning loop 203 above hook 202 and distal tip 304 of hook insertion needle 302. Flexible needle 306 can then be retracted back into said insertion tube 307 (FIG. 3D), leaving loop 203 inside the tissue above hook 202.

At the next stage (FIG. 3E), hook insertion needle 302 is advanced further into the tissue while inserting hook 202 through loop 203. In this stage, tension is applied at suture 200, which causes loop 202 the tighten around said needle 302.

At the next stage (FIG. 3F), hook insertion needle 302 is retracted, leaving hook 202 located inside said loop 203.

At the final stage (FIG. 3G), both of hook insertion needle 302 and loop insertion needle 303 are removed from the tissue. Additional tension can be applied the suture 200, causing further tightening of loop 203 and leaving suture 200 secured inside the tissue.

In certain embodiments, a reticulation of the distal end of suture applicator 100 allows the distal tip to be rotated around its longitudinal axis. This can allow the application of sutures in various orientation in respect to said suture applicator 100.

Figure 4A:
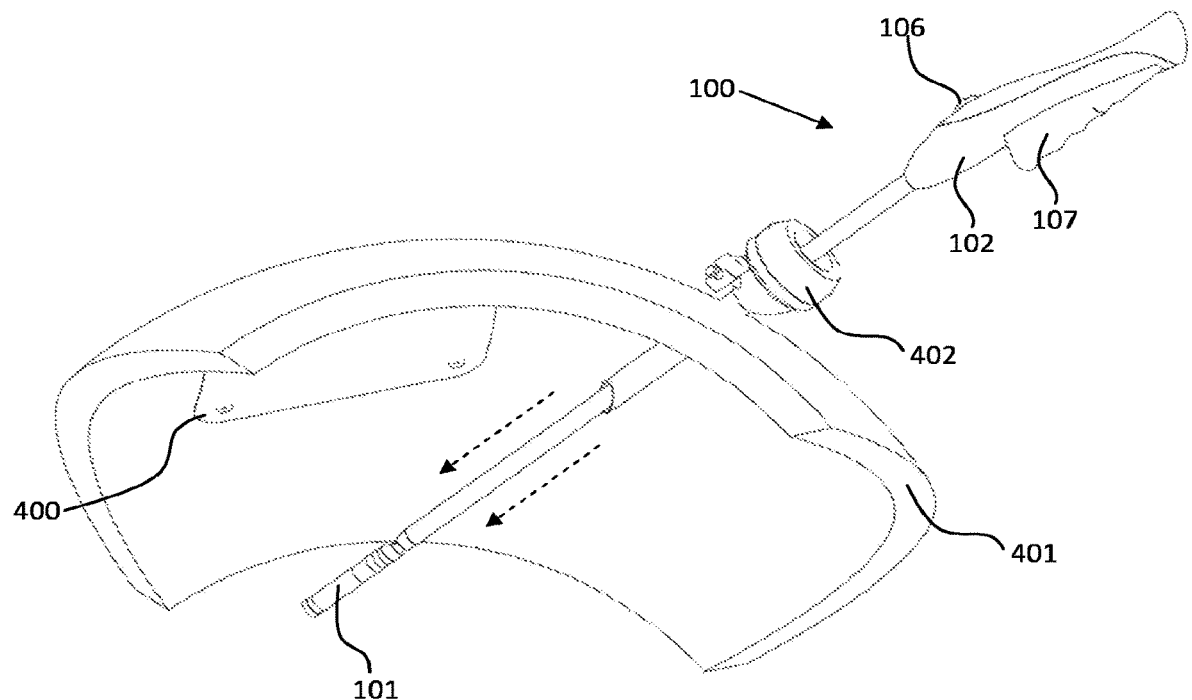
FIGS. 4A-4D illustrate fixating a hernia mesh to an abdominal wall.
Figure 4B:
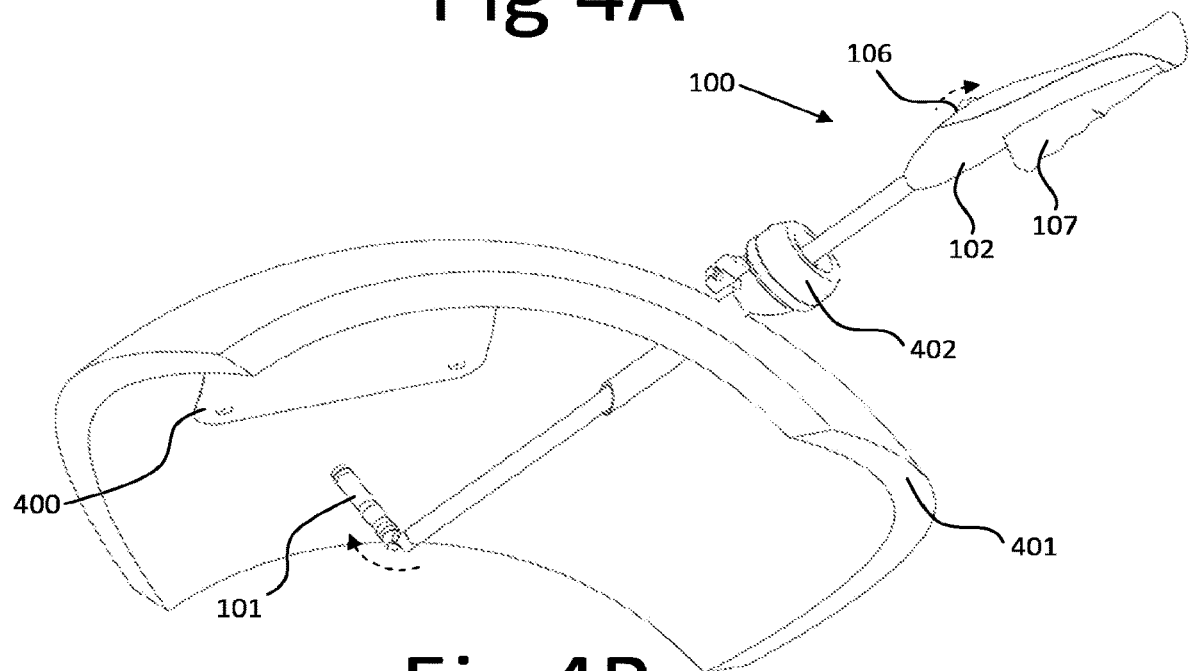
Figure 4C:
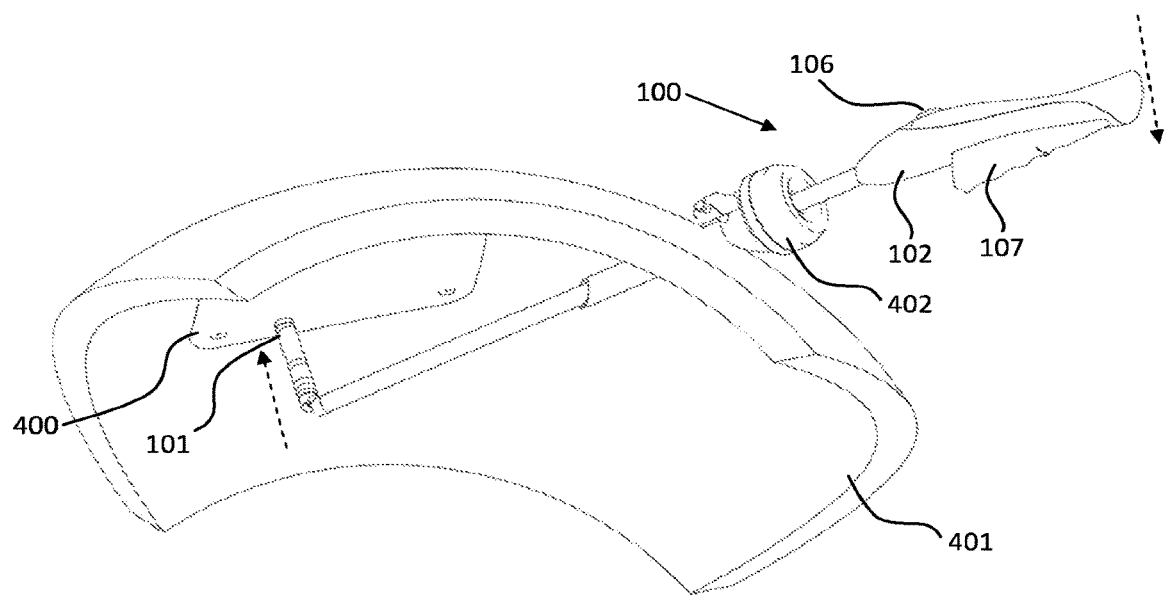
Figure 4D:
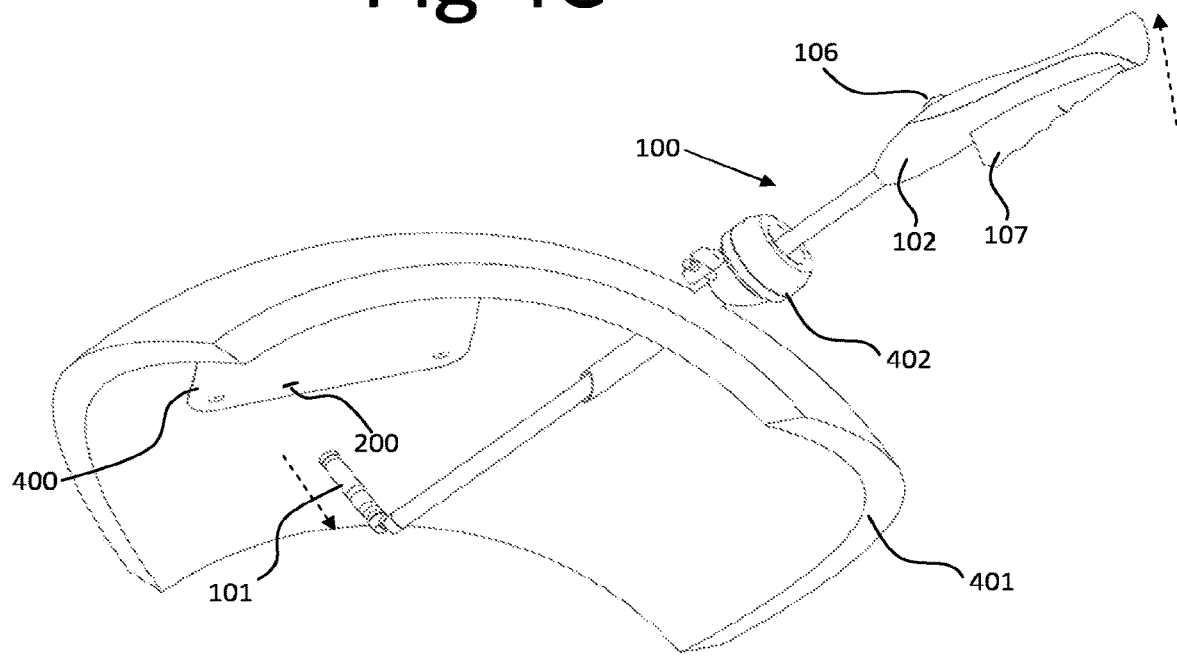

Reference is now made to FIGS. 4A-4D, which illustrates use of suture applicator 100 for securing a hernia mesh 400 to the abdominal wall 401 during laparoscopic hernia repair surgery. In certain aspects, the invention provides devices and methods for securing mesh 400 to tissue. Methods include inserting a distal portion of suture applicator 100 into a patient's abdominal cavity through a trocar 402 or through an incision (FIG. 4A). Applicator section 101 can be articulated via articulation knob 106 (FIG. 4B). Distal tip 301 is pressed against hernia mesh 400 (FIG. 4C) and a single suture is delivered through the tissue and hernia mesh 400 and secured in place by pressing lever 107 on handle 102. Tip 301 is then removed as shown in FIG. 4D.

Figure 5A:
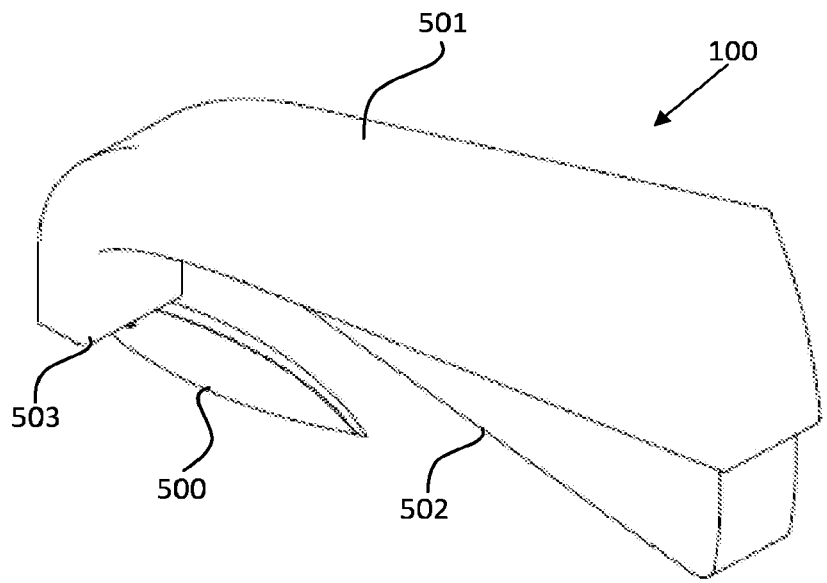
FIGS. 5A-5B illustrate use of the suture applicator for wound closure applications.
Figure 5B:
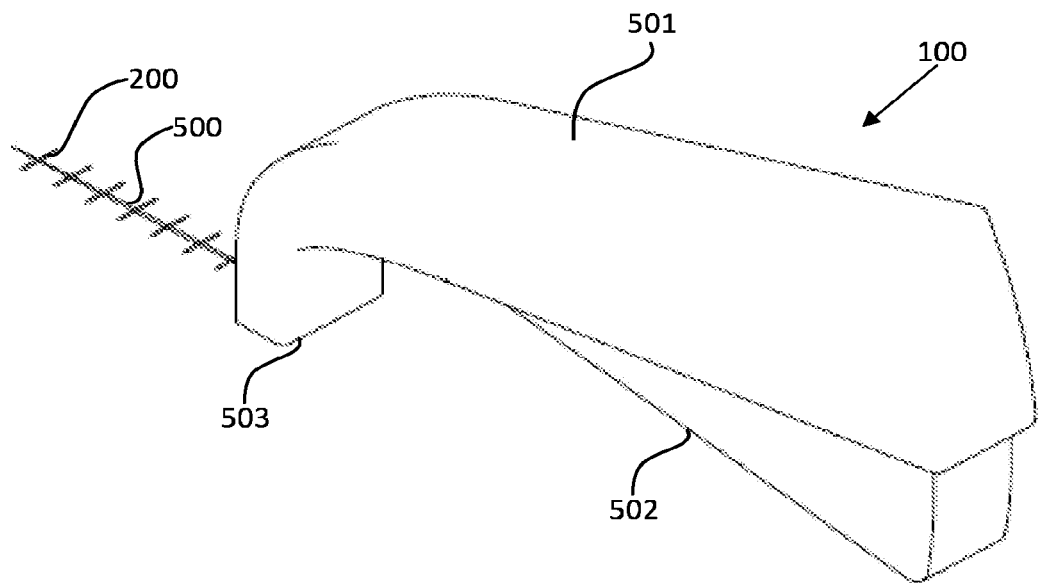

Reference is now made to FIGS. 5A-5B which show use of suture applicator 100 for closure of wound 500. According to this embodiment, suture applicator 100 comprises a body 501 and activation lever 502 adapted to initiate suture application by the user. According to this embodiment, a wound is closed by pressing the distal tip 503 of suture applicator 100 to wound 500 (FIG. 5A) and applying at least one suture 200 through both sides of said wound 500 (FIG. 5B).

FIGS. 6A-6H illustrate a mechanism of action for wound closure. The process is similar to the one shown in FIGS. 3A-3G, however it includes a step for bringing two sides of a wound together before securing suture 200 to the tissue. For illustration purposes, the tissue and the wound is not shown in these drawings.

Figure 6A:
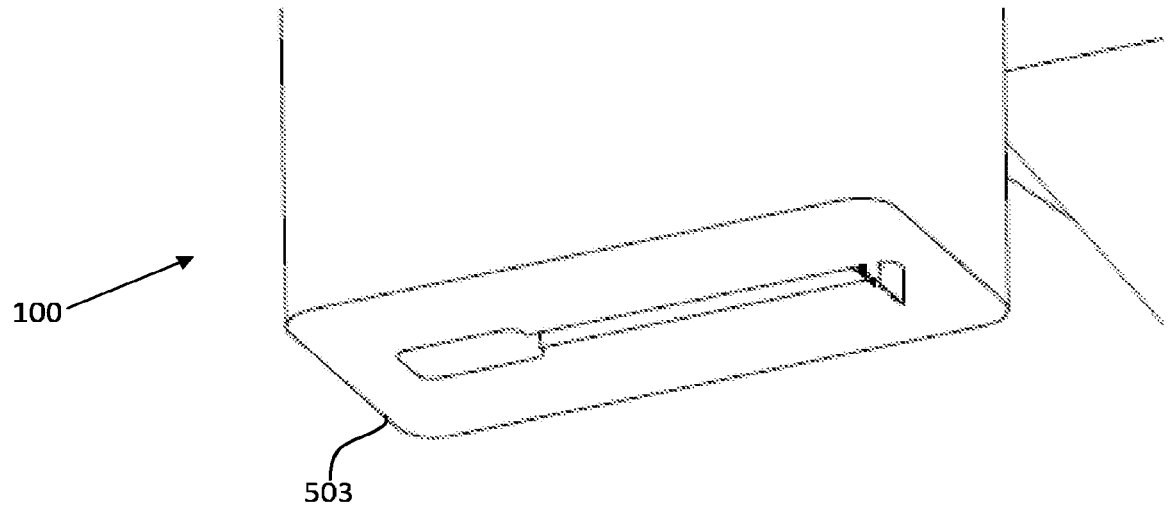
FIGS. 6A-6H illustrate application of a suture during wound closure operation.
Figure 6B:
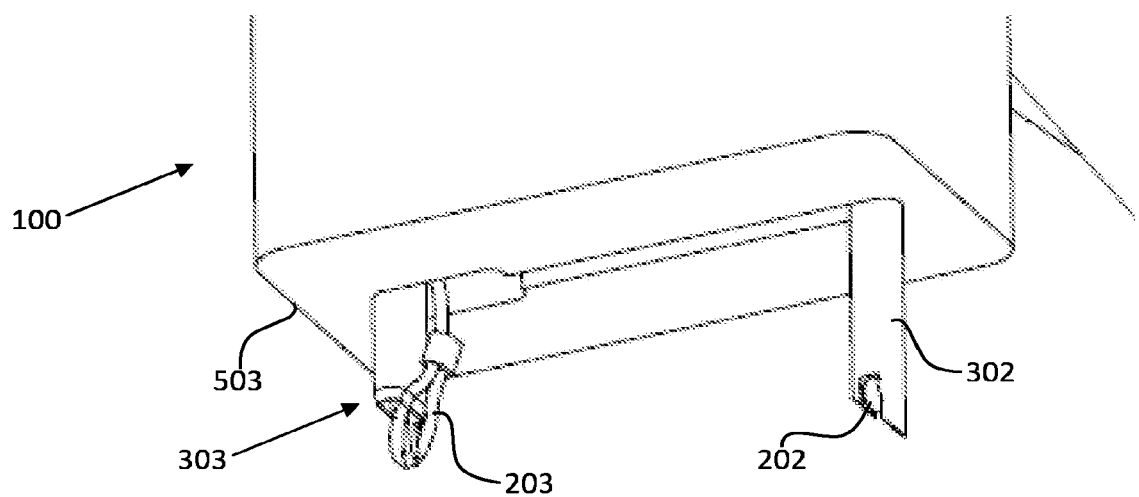
Figure 6C:
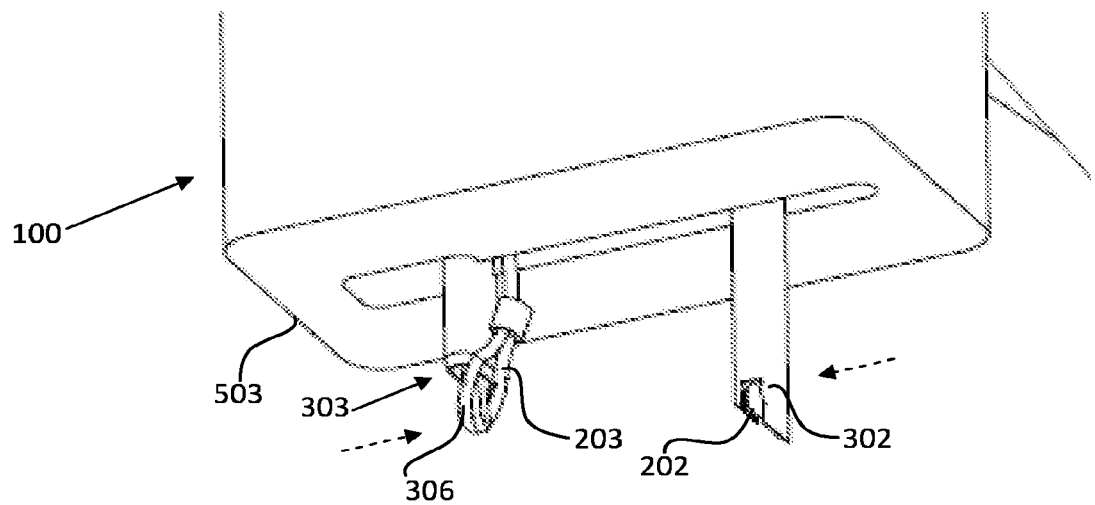
Figure 6D:
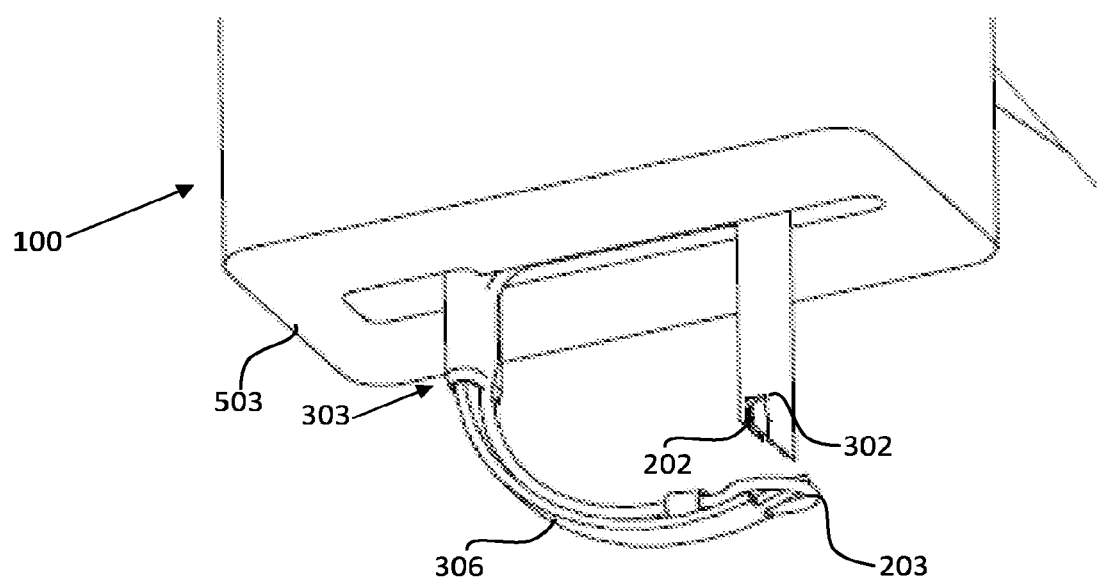
Figure 6E:
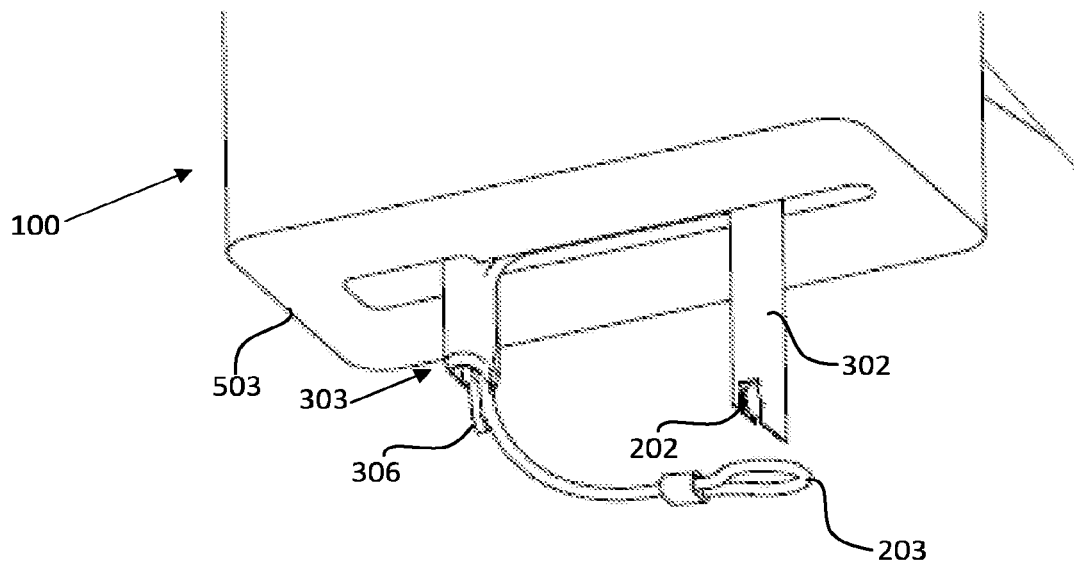
Figure 6F:
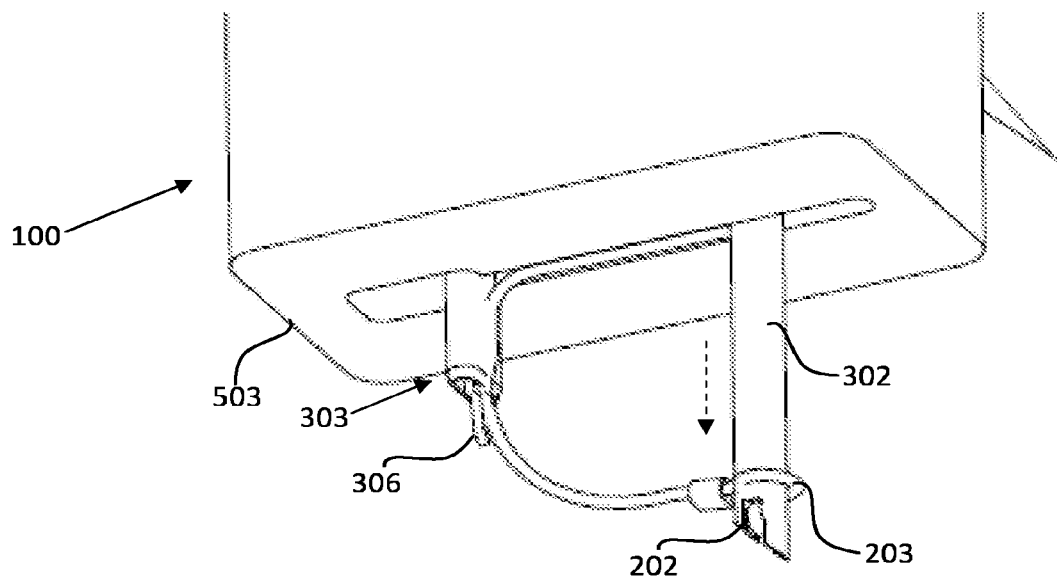
Figure 6G:
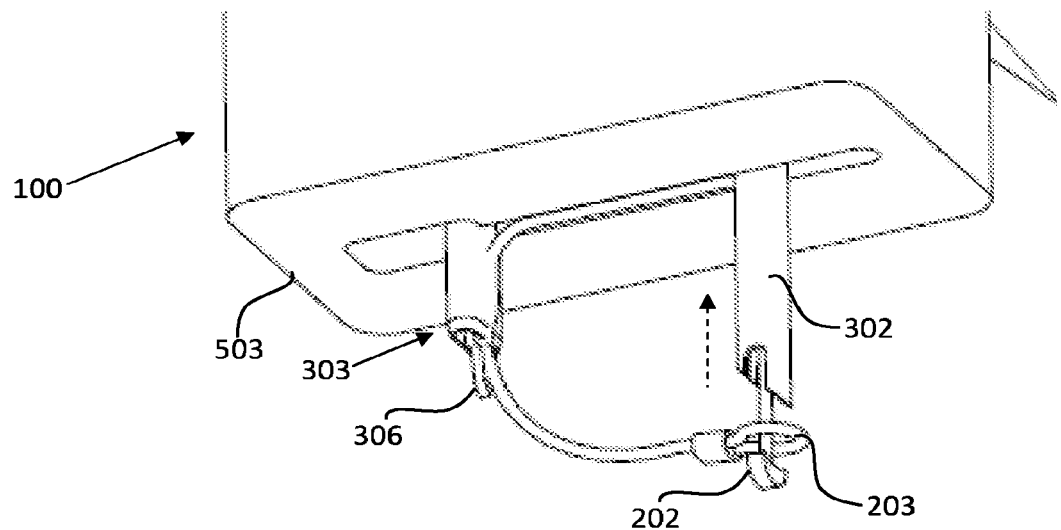
Figure 6H:
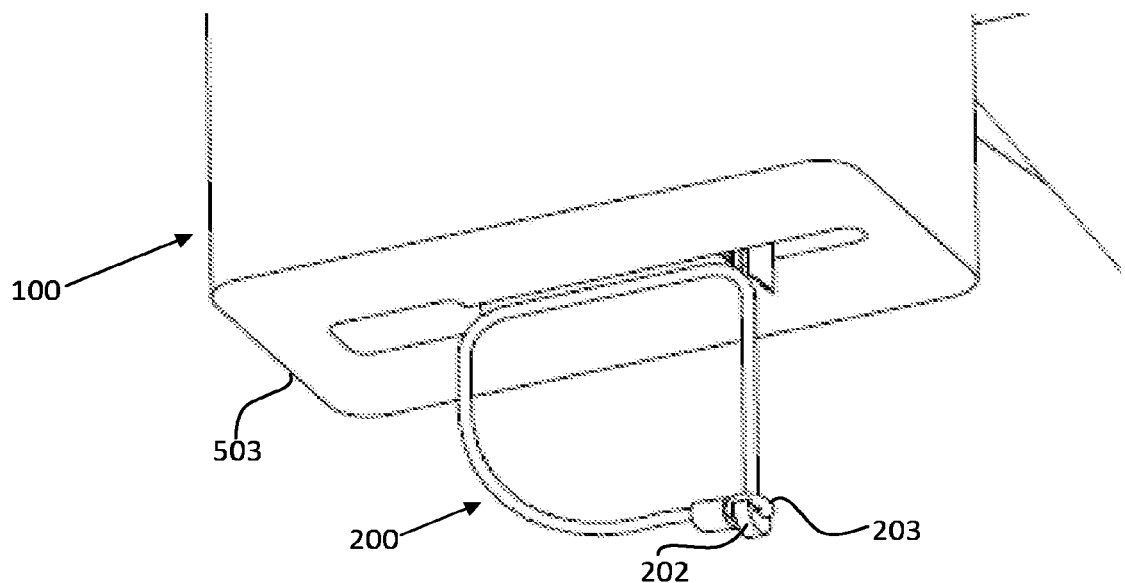

At the first stage (FIG. 6A), distal tip 503 of suture applicator 100 is pressed against the tissue with wound 500 located roughly at the center of said distal tip 503. Next, hook insertion needle 302 and loop insertion needle 303 are inserted to the tissue together with suture 200 (FIG. 6B) Then, the two needles 302 and 303 are brought together, bringing the sides of the wound together (FIG. 6C). Then, as shown in FIGS. 6D-6H, the suture is applied and secured in a similar way as described above in reference to FIGS. 3C-3G, resulting in suture 200 passing thorough both sides of wound 500, thus closing the wound.

In certain embodiments, suture applicator 100 can hold at least one and preferably two or more of suture 200. Once one suture is applied to the tissue, another suture 200 is loaded on hook insertion needle 302 and loop insertion needle 303 in preparation to the next suture application.

Suture applicator 100 can be disposable or reusable. In the first case, suture applicator 100 is delivered together with one or more of suture 200 and disposed of after use. If suture applicator 100 is reusable, it is adapted for re-sterilization and sutures can be provided separately in a cartridge than can be loaded before or during the operation. The cartridge can provide parts of the suture application mechanism (e.g. applicator section 101, insertion needles 302, 303).

A suture 200 can pass through the entire thickness of the tissue or can be embedded inside the tissue. Further, suture 200 can be applied manually, without the use of suture applicator 100. To apply suture 200 manually, a suturing needle is attached to either of or both of the ends of suture 200 and used to insert suture 200 into tissue.

While described above in reference to FIGS. 2A and 2B as having a generally wire-like structure in which loop 203 can be made smaller by a cinching action through loop holder 204, a suture according to the invention can have other structures and forms.

Figure 7A:
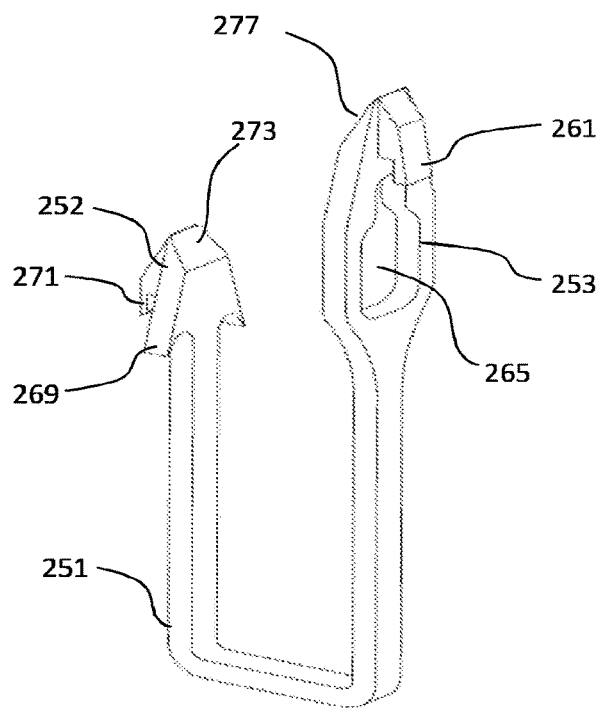
FIGS. 7A-7C show a suture according to certain embodiments.
Figure 7B:
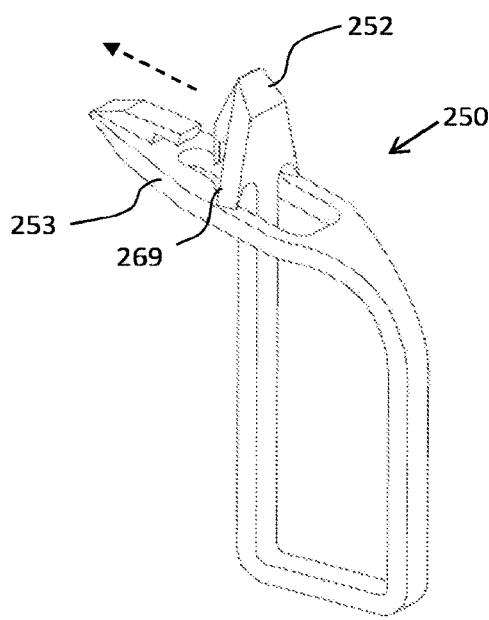
Figure 7C:
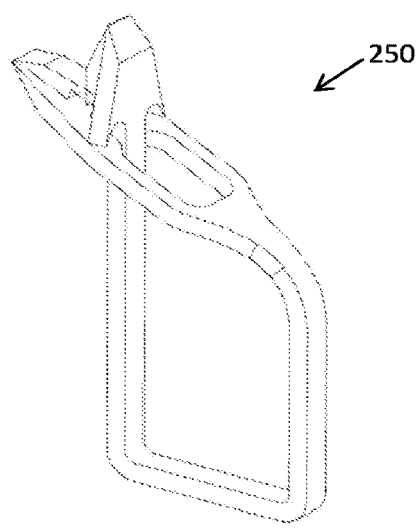

FIGS. 7A-7C show a suture 250 according to certain embodiments. In certain embodiments, the suture is integrally formed. Suture 250 generally includes a body member 251 having a first member 253 at one end and a second member 252 at the other. As shown in FIGS. 7A-C, first member 253 includes a hook and second member 252 includes a loop.

Suture 250 further includes needle interface hook 261 at the loop end, and a hook-side needle interface hook 271 at the hook end. The loop end is characterized by aperture 265, that narrows towards the end of suture 250, i.e., the aperture has a wide section and a narrow section, the narrow section being distal to the wide section. Loop end further has insertion slope 277 and hook-side insertion slope 273, which can be, for example, beveled tips, to aid insertion of suture 250 through tissue.

Suture 250 generally includes at least one barb 269 at the hook end. When the hook end is inserted through aperture 265, as shown in FIG. 7B, one or more of barb 269 (two are shown) tend to prevent retraction of the hook end out of and away from the loop end. As shown in FIGS. 7A-7C, each of barbs 269 has a fin-like structure and is adapted to be bent during insertion. Further, in certain embodiments, aperture 265 of first member 253 is dimensioned to be not substantially larger than second member 252. For example, the width defined by one or more of barb 269 can be greater than the width defined by aperture 265 at its widest point. Insertion of second member 252 through aperture 265 generally involves either of second member 252 or first member 253 deforming slightly for insertion. The fin-like structure of barb 269 can bend towards body 251, first member 253 can stretch, first member 253 and second member 252 can twist relative to one another, or a combination thereof. Deformation can be elastic (return to original conformation) or plastic or a combination thereof.

As shown in FIG. 7B, tension on suture 250 will tend to slide second member 252 towards the narrow portion of aperture 265. This results in the locked conformation illustrated in FIG. 7C, in which the stem part of second member 252 (e.g., a portion substantially similar in cross section to that of body member 251) is slid into and occupies the narrowest part of aperture 265. This serves to lock suture 250 into a closed conformation.

As shown in FIG. 7A, second member 252 can include needle interface hook 271 while the loop-end includes loop interface hook 261. Needle interface hook 271 and loop interface hook 261 are illustrated as protrusions that generally taper to be smaller extending towards an end of suture 250. As shown in FIG. 7A, these interface hooks include a back portion that presents a push-able surface towards the main body portion of suture 250. In certain embodiments, one or both of these push-able surfaces are presented by indentations into suture 250 or other structures. The function of needle interface hook 271 and loop interface hook 261 are illustrated in FIGS. 8A and 8B.

Figure 8A:
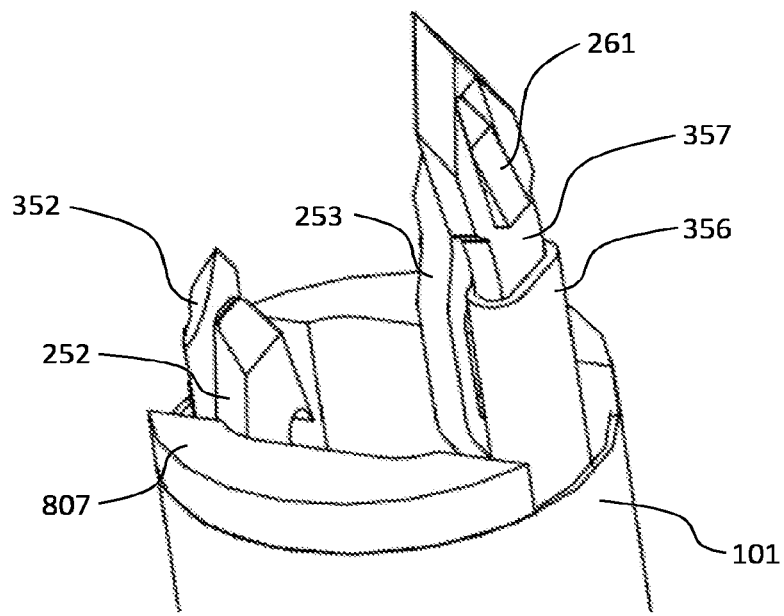
FIGS. 8A and 8B illustrate operation of a delivery tip of a suturing device.
Figure 8B:
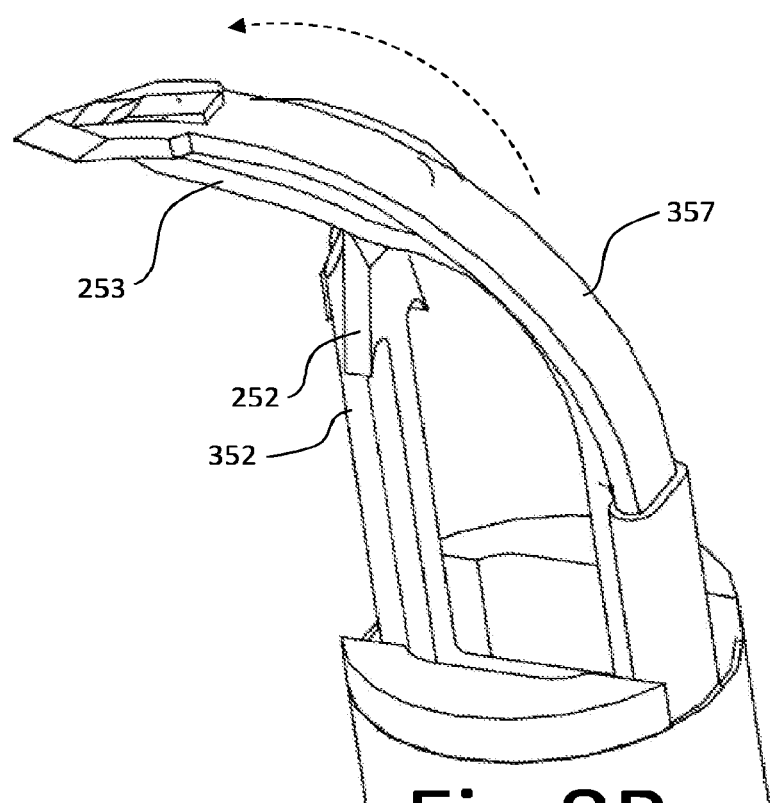

As shown in FIGS. 8A and 8B, the delivery tip of applicator section 101 of suture applicator 100 provides a mechanism for delivering suture 250 to tissue and fastening it there. Hook insertion needle 352 is slidably disposed within applicator section 101 and configured to interface with second member 252 via needle interface hook 271. Loop insertion needle 357 extends from insertion tube 356 and similarly interacts with first member 253 via loop interface hook 261. As shown in FIG. 8A, applicator section 101 optionally includes a spacer 807 to assist in precise positioning of suture 250.

FIG. 8B in combination with FIG. 8A illustrates the coordinated functioning of the insertion needles of applicator section 101. As shown in FIGS. 8A and 8B, hook insertion needle 352 has and maintains a substantially straight conformation as it assists in driving a hook end of suture 250 into tissue. Loop insertion needle 357 has a shape memory material such that, when the needle is contained within applicator section 101, the needle exhibits a shape substantially similar to, or governed by, a shape of applicator section 101. When loop insertion needle 357 is extended out from applicator section 101, loop insertion needle exhibits a curved shape (FIG. 8B).

Applicator section 101 is configured to deliver suture 250 by pushing each of its ends into tissue. Delivery is coordinated by the independent translation of push rods (not shown in FIGS. 8A and 8B) operably coupled to hook insertion needle 252 and loop insertion needle 357. Coordination of delivery involves extending hook end of suture 250 away from applicator section 101 while also extending loop end of suture 250 and bringing the two ends of the suture together (e.g., through the operation of a shape memory material in loop insertion needle 357).

In certain embodiments, a leading edge of either or both of the insertion needles is at least partially sharpened to aid in penetration of tissue. Each of needle interface hook 271 and loop interface hook 261 can have a back surface that gets pushed by the corresponding insertion needle. Alternatively or additionally, either needle interface hook can include a slot and a portion of the corresponding insertion needle can be dimensioned to engage the slot. By these means, the needles can drive suture 250 into tissue and when the insertion needles are retracted, they disengage with suture 250 leaving it in place and fastened in a closed loop.

Figure 9A:
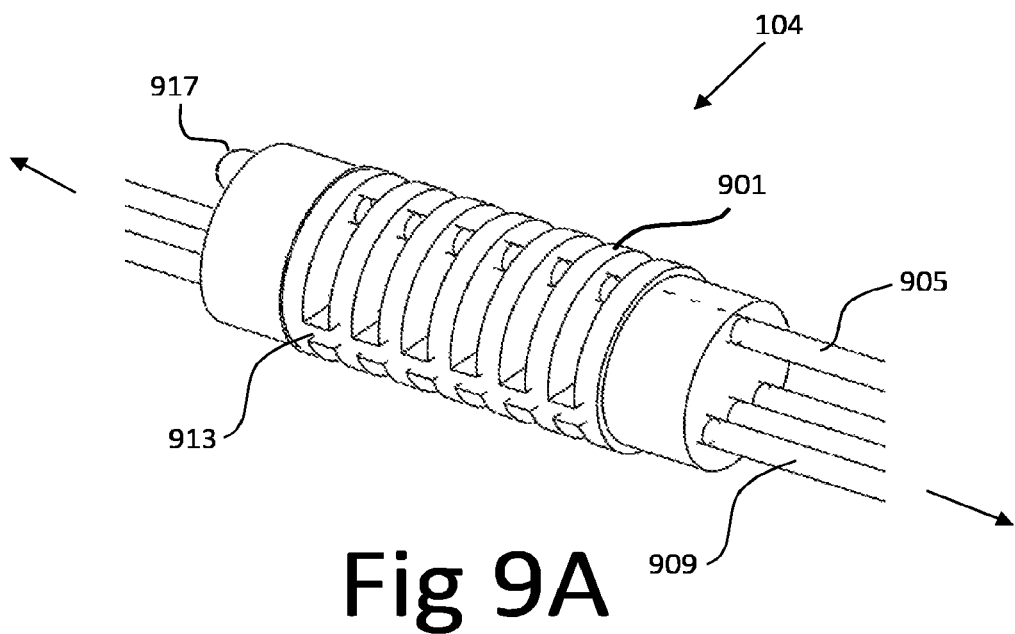
FIGS. 9A and 9B show an articulation joint.
Figure 9B:
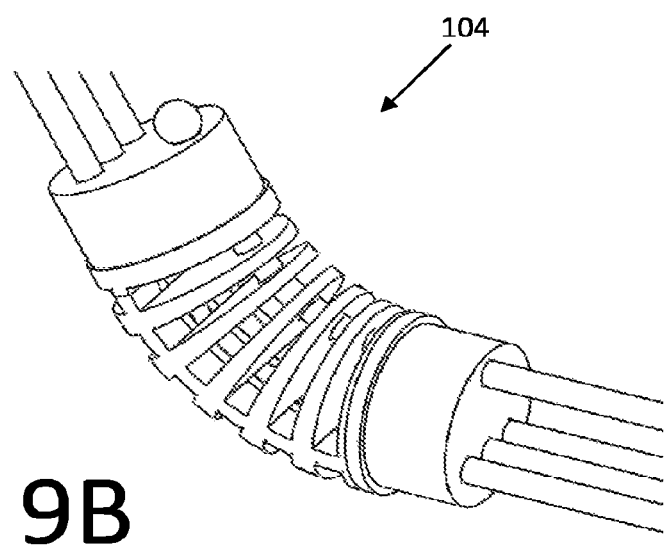

With reference to FIG. 1B, applicator section 101 and shaft 103 can include articulation joint 104. FIGS. 9A and 9B show a structure by which articulation joint 104 can allow shaft 103 to bend while still operating according to the embodiment described herein. As shown in FIG. 9A, articulation joint 104 includes a plurality of living hinge 913. A living hinge 903 generally includes a flexible portion and a flange 901. One or more of push rod 909 extend through joint 104 generally disposed so that, where there are multiple push rods, an axis of each push rod exhibits the same radius as the others when hinge 104 is bent. Flange 901 can be provided to limit the radius of curvature of hinge 104 to optimize functionality of applicator section 101, for example, by preventing the push rods from being bent too much.

Hinge 104 further includes an articulation cable 905 with an articulation wire ending 917 disposed on a distal side of hinge 104 from handle 102 (not pictured). When articulation wire 917 is pulled by a mechanism in handle 102 (discussed in more detail below), articulation wire ending 917 exhibits a compressive force on hinge 104, causing it to compress on one side, while expanding on the other, thus forming a bend in shaft 103, as shown in FIG. 9B.

Articulation joint 104 can be made with any suitable material known in the art such as, for example, an elastically deformable material. In certain embodiments, the material is a low friction material such as PTFE to minimize friction between joint 104 and push rod 909.

Suture applicator is designed and dimensioned for use in laparoscopic or endoscopic surgery. Shaft 103 is dimensioned for use with endoscopic tubes and apparatuses. The device can also be inserted through an incision or trocar and used within a body.

In certain embodiments, suture applicator 100 can hold at least one of suture 250 in a cartridge 801 that can be interchangeably loaded into applicator section 101 of suture applicator 100.

Figure 10:
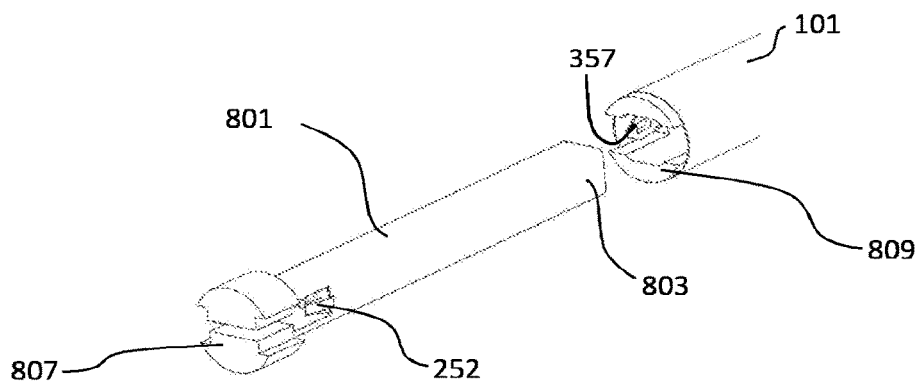
FIG. 10 shows a suture cartridge.

FIG. 10 shows a cartridge 801 having an insertion end 803 and a spacer 807 oriented for insertion into applicator section 101. At the end of applicator section 101, FIG. 10 shows receiving pad 809 with loop insertion needle 357 visible disposed therein. As can be seen depicted in the distal end of cartridge 101, second member 252 (specifically, a portion of needle interface hook 271) is held in a slot, oriented to interface with hook insertion needle 352 in applicator section 101 (not visible in FIG. 10). Receiving pad 809 can include an interior shape dimensioned to receive insertion end 803.

Cartridge 801 has a structure that cooperates with the mechanical structure of suture applicator 100 so that the device can deliver and fasten sutures within a body of a patient. Cartridge 801 accommodates sutures of different sizes.

In some embodiments, cartridge 801 uses an interchangeable spacer and spacers of different sizes accommodate different sutures. In certain embodiments, each cartridge holds a number of sutures of the same size. Spacers are provided to control the distance between the tip of the device and the tissue (or prosthesis) surface. For example, for smaller sutures, a larger spacer is provided to prevent the suture from penetrating too deeply into the tissue. Similarly, for larger sutures, a smaller spacer allows for good penetration depth of the suture.

Figure 11:
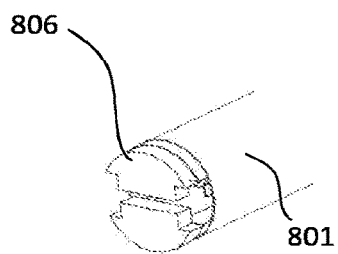
FIGS. 11-13 show suture cartridges for use with different sized sutures.
Figure 12:
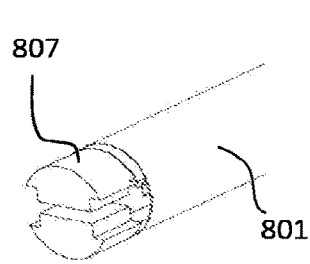
Figure 13:
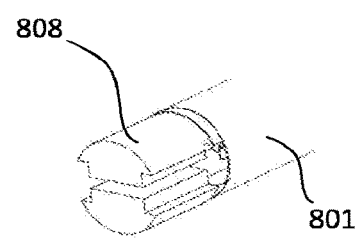

FIG. 11 shows a thin spacer 806 for use with larger sutures. In some embodiments, the spacers are not interchangeable but instead formed as part of a disposable cartridge 801. FIG. 12 shows a spacer 807 for use with intermediate sutures. FIG. 13 shows a long spacer 808 for use with small sutures. As shown in FIGS. 10-13, a spacer may include a suture release slot disposed at an end of the body of the cartridge. In certain embodiments, cartridge 801 can be inserted into an end of an shaft 103 via insertion end.

As can be seen in FIG. 10, when cartridge 801 is inserted into shaft 103, second member 252 makes contact with hook insertion needle 352 via needle interface hook 271 and first member 253 makes contact with loop insertion needle 357. Suture 250 is delivered to tissue by the action of push rods that drive the insertion needles. Each push rod, and thus each needle, translates parallel to an axis of shaft 103 relative to each other as well as to member 103. In a preferred embodiment, said sutures are stacked one on top of the other inside cartridge 801; during each suture application cycle, a single suture is connected to the said insertion needles and then inserted into the tissue. At the end of the application cycle, a suture is advanced to the top of the cartridge in preparation to the next application cycle. In another embodiment cartridge 801 includes an indicator which visually indicates to the surgeon when the cartridge is almost empty (e.g. 1 or 2 sutures remains in the cartridge) and or completely empty. Motion of the push rods is governed by the mechanical structure of applicator 100.

Figure 14:
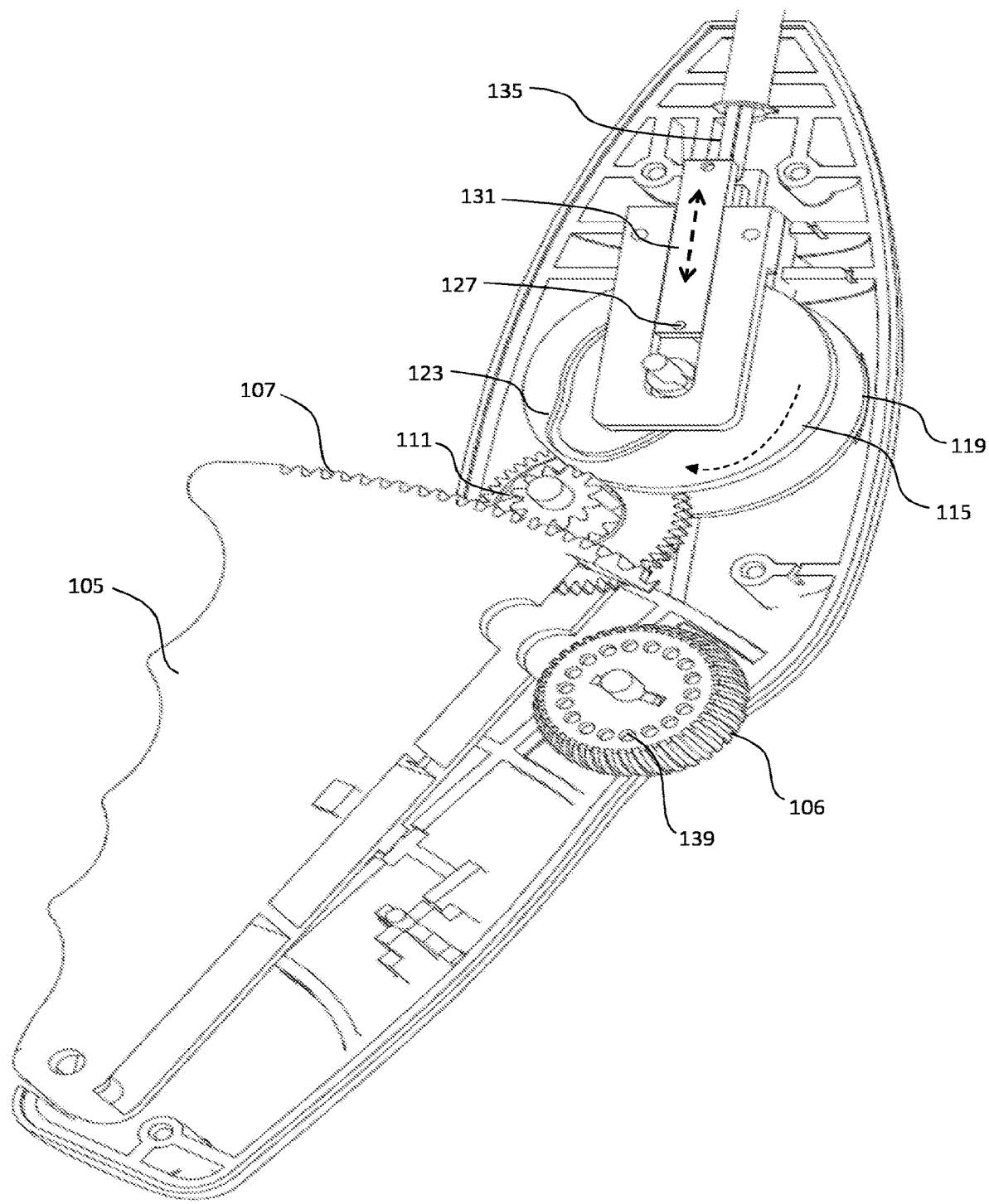
FIG. 14 gives a view of components of a handle of a suturing device.

FIG. 14 gives a view of components of a handle of a suturing device. As can be seen in FIG. 14, one or more of push rod 135 are linked to one or more of translator bar 131. Translator bar 131 has a pin 127 fixed into a slot 123 of slot wheel 115. As shown in FIG. 14, applicator 100 includes a second slot wheel 119. Additional slot wheels (not shown) may be included. The rotation of the slot wheel is driven through gear mechanism 111 by a geared face 107 of trigger 105.

By the relationship of these parts, when trigger 105 is squeezed, each of the slot wheels rotate. Because each slot (e.g., slot 123) is irregularly shaped (e.g., not a circle concentric with slot wheel 115), the corresponding translator bar translates independently relative to handle 102 and with acceleration defined by the disposition of the slot. The independent translation of translator bar 131 causes the independent translation of push rod 135 which (looking back at FIGS. 8A and 8B) cause the independent action of hook insertion needle 352 and loop insertion needle 357, as described above.

In certain embodiments, the series of coordinated motions of the insertion needles, and the delivery of a suture, is operated and coordinated electronically. For example, applicator device 100 can include servomotors operably connected to a governing circuit and/or chip. A motor can drive the slot wheels. Or, motors can drive each push rod as governed by a chip executing instructions provided, for example, by a tangible, non-transitory computer memory such as, for example, a field-programmable gate array or a disc drive.

Where shaft 103 includes articulation joint 104, articulation knob 106 controls the flexure of joint 104. Knob 106 is rotated by a user (e.g., with a thumb). During the rotation, articulation cable 905 (shown in FIGS. 9A and 9B) is wrapped around the knob's axis, pulling it toward the handle, articulating joint 104. Knob 106 can include one or more of socket 139 adapted to fit a ball plunger in place once a desired degree of articulation is obtained.

The invention further provides methods for closing a wound that involve deploying suturing device 100 to deliver a suture to a wound. Wound closure according to methods of the invention involves positioning the delivery tip close to the wound. Where the wound is inside the body, the shaft 103 is inserted through an incision, trocar, or endoscopic channel. A suture is delivered and formed into a closed configuration by device 100.

When a practitioner depresses trigger 105, loop insertion needle 357 extends from insertion tube 356 and interacts with first member 253 via loop interface hook 261. Hook insertion needle 352 has and maintains a substantially straight conformation as it assists in driving a hook end of suture 250 into tissue. When loop insertion needle 357 is extended out from applicator section 101, it curves to guide the fastening of the suture.

Suture 250 is delivered by pushing each of its ends into tissue. Delivery is coordinated by the independent translation of push rods operably coupled to hook insertion needle 252 and loop insertion needle 357, which is triggered through the use of trigger 105. Coordination of delivery involves extending hook end of suture 250 away from applicator section 101 while also extending loop end of suture 250 and bringing the two ends of the suture together (e.g., through the operation of a shape memory material in loop insertion needle 357). Methods include using the needles to drive suture 250 into tissue and retracting the needles so they disengage from suture 250 leaving it in place and fastened in a closed loop, closing the wound.

The invention also provides methods for securing a medical prosthesis to tissue. Securing the prosthesis is accomplished through delivering a suture to a target tissue that has a prosthesis applied to it, using applicator 100. Methods include inserting a distal portion of suture applicator 100 into a patient's abdominal cavity through a trocar or through an incision. The distal end is pressed against the hernia mesh and a suture is delivered through the tissue and hernia mesh and secured in place by pressing trigger 105 on handle 102. Shaft 103 is then removed.

Delivery according to the methods of the invention causes the first end of the body to mate with and be retained by the second end of the body, thereby forming the suture into a closed configuration and securing the prosthesis to the tissue. The prosthesis can be secured by employing a fastening structure provided by the first and second members.

During delivery, hook insertion needle 352 interfaces with second member 252 via needle interface hook 271. Loop insertion needle 357 extends from insertion tube 356 and similarly interacts with first member 253 via loop interface hook 261.

Loop insertion needle 357 is extended out from applicator section 101 and curves to guide the suture through the prosthesis. Delivery is coordinated by the independent translation of push rods (discussed above) operably coupled to hook insertion needle 252 and loop insertion needle 357. Coordination of delivery involves extending hook end of suture 250 away from applicator section 101 while also extending loop end of suture 250 and bringing the two ends of the suture together (e.g., through the operation of a shape memory material in loop insertion needle 357). Methods can include pushing a suture through a back surface of needle interface hook 271 and loop interface hook 261 with a corresponding insertion needle. By these means, the needles can drive suture 250 into the prosthesis (e.g., hernia mesh). The needles are then retracted, leaving suture 250 in place and fastened in a closed loop securing the prosthesis to the tissue.

Figure 15A:
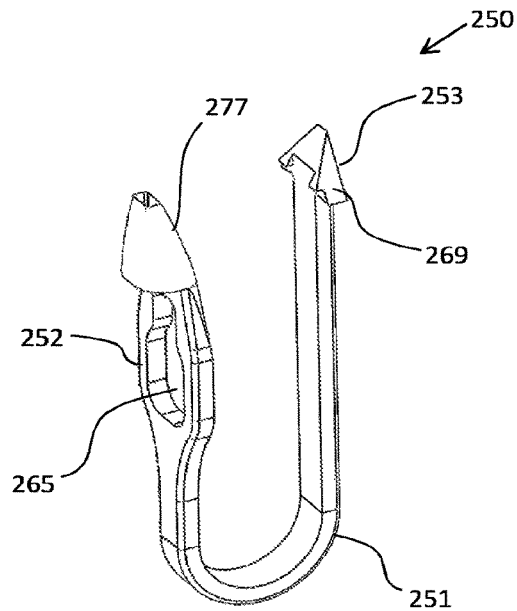
FIGS. 15A-15C depict a suture according to certain embodiments.
Figure 15B:
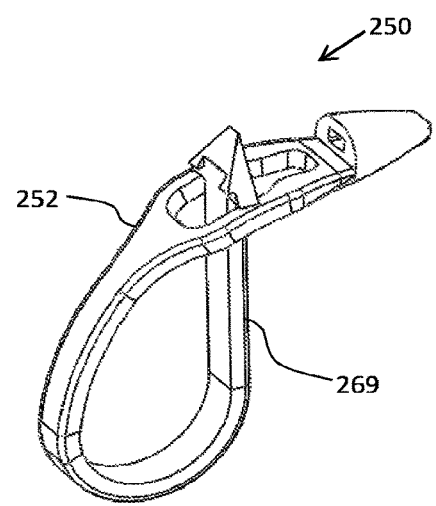
Figure 15C:
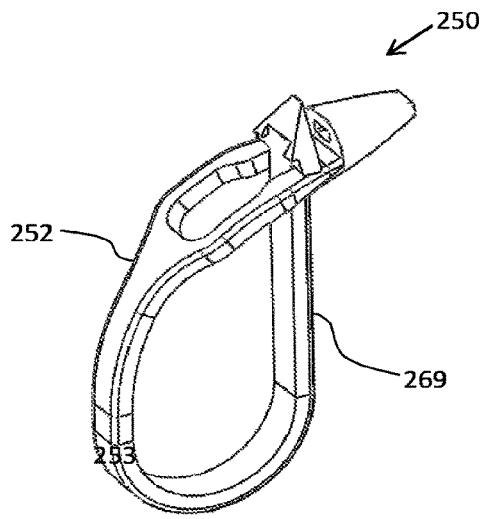
Figure 16:
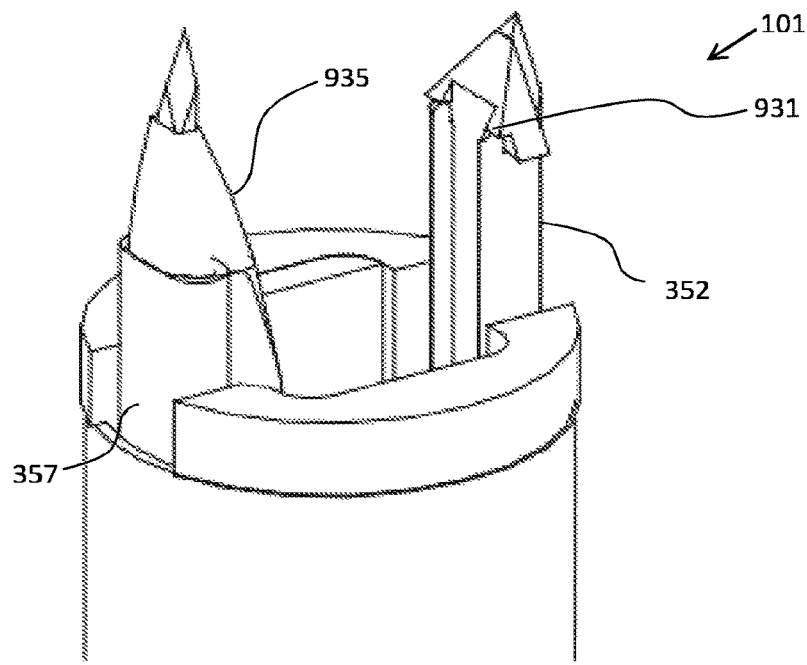
FIGS. 16 and 17 depict a applicator section.
Figure 17:
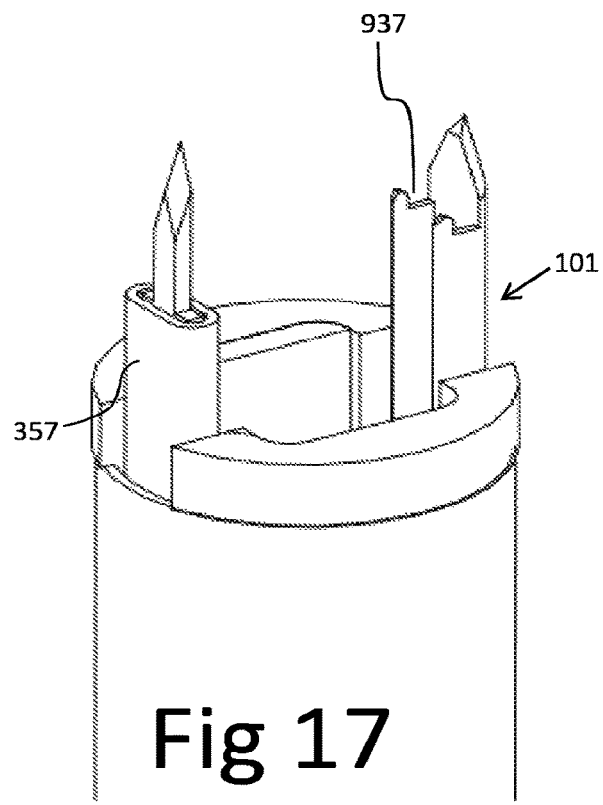

FIGS. 15A-15C depict a suture 250 according to certain embodiments. FIG. 15A shows suture 150 in an open configuration, while FIG. 15B shows suture 250 in a closed configuration. FIG. 15C shows suture 250 in a locked configuration. Suture 250 includes insertion slope 277 and at least one barb 269 that are dimensioned to operate with hook insertion needle 352 and loop insertion needle 357 of the embodiment shown in FIGS. 16 and 17. First member 253 includes a hook and second member 252 includes a loop FIG. 16 shows a suture applicator with suture 250 according to certain embodiments. FIG. 17 shows the suture applicator of FIG. 16, without a suture 250. FIG. 16 shows loop insertion needle 357 and hook insertion needle 352. As shown in FIG. 16, the needle integration section 935 is shaped as a continuation of the needle tip in order to a allow penetration through the mesh and the tissue layers. Specifically, suture 250 includes insertion slope 277 and the applicator includes a sloped needle integration section 935 that are dimensioned to cooperate to provide a substantially smooth, continual slope. Bulges 931 prevent the mesh fibers and the tissue from being caught between suture 250 and hook insertion needle 352. As shown in FIG. 17, slot 937 is operable to hold the hook side of suture 250 in place during penetration, e.g., by engaging barbs 269.

Figure 18A:
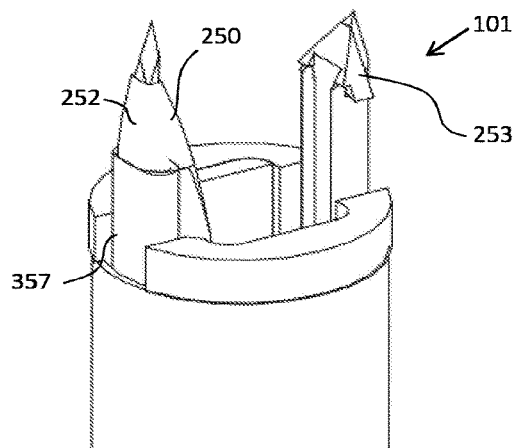
Figure 18B:
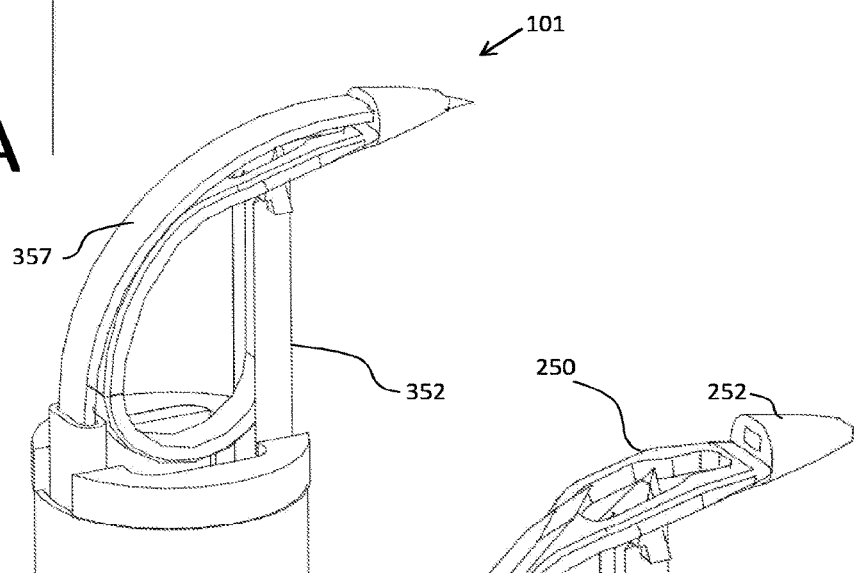
Figure 18C:
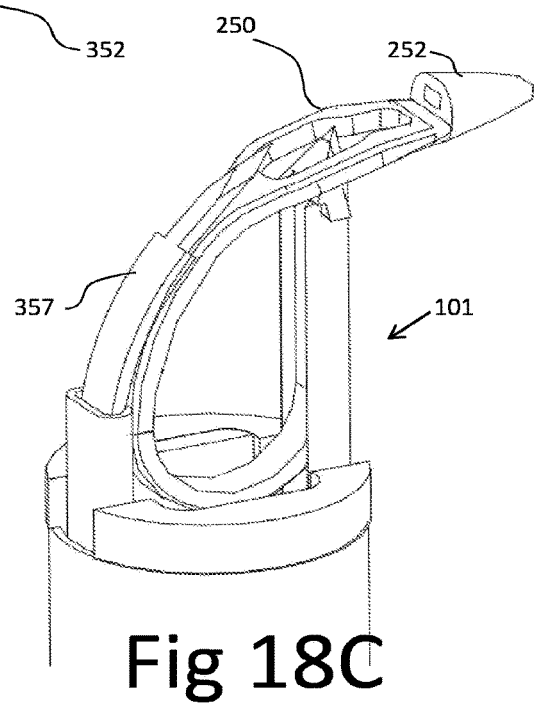

FIGS. 18A-18F depict the operation of applicator section 101 of the suture applicator depicted in FIGS. 16 and 17. FIG. 16A shows an initial stage of operation. Hook insertion needle 352 and loop insertion needle 357 are fully engaged with first member 253 and second member 252, respectively, of suture 250. As seen in FIG. 18B, the loop is fully deployed and the hook partially penetrates the loop. In FIG. 18C, hook insertion needle 352 holds the loop in place while the loop insertion needle 357 is retracted.

FIGS. 18D-18F show locking and release of suture 250. FIG. 18D shows hook insertion needle 352 pushing the hook through the loop. As shown in FIG. 18E, since the hook is slightly wider than the loop's wide section, first member 253 is caught in second member 252 and removed from the hook insertion needle 352 once hook insertion needle 352 is retracted. FIG. 18F shows that, once tension is applied on the clip, the hook slides to the narrow section of the hook. In this stage the clip is locked.

Figure 19:
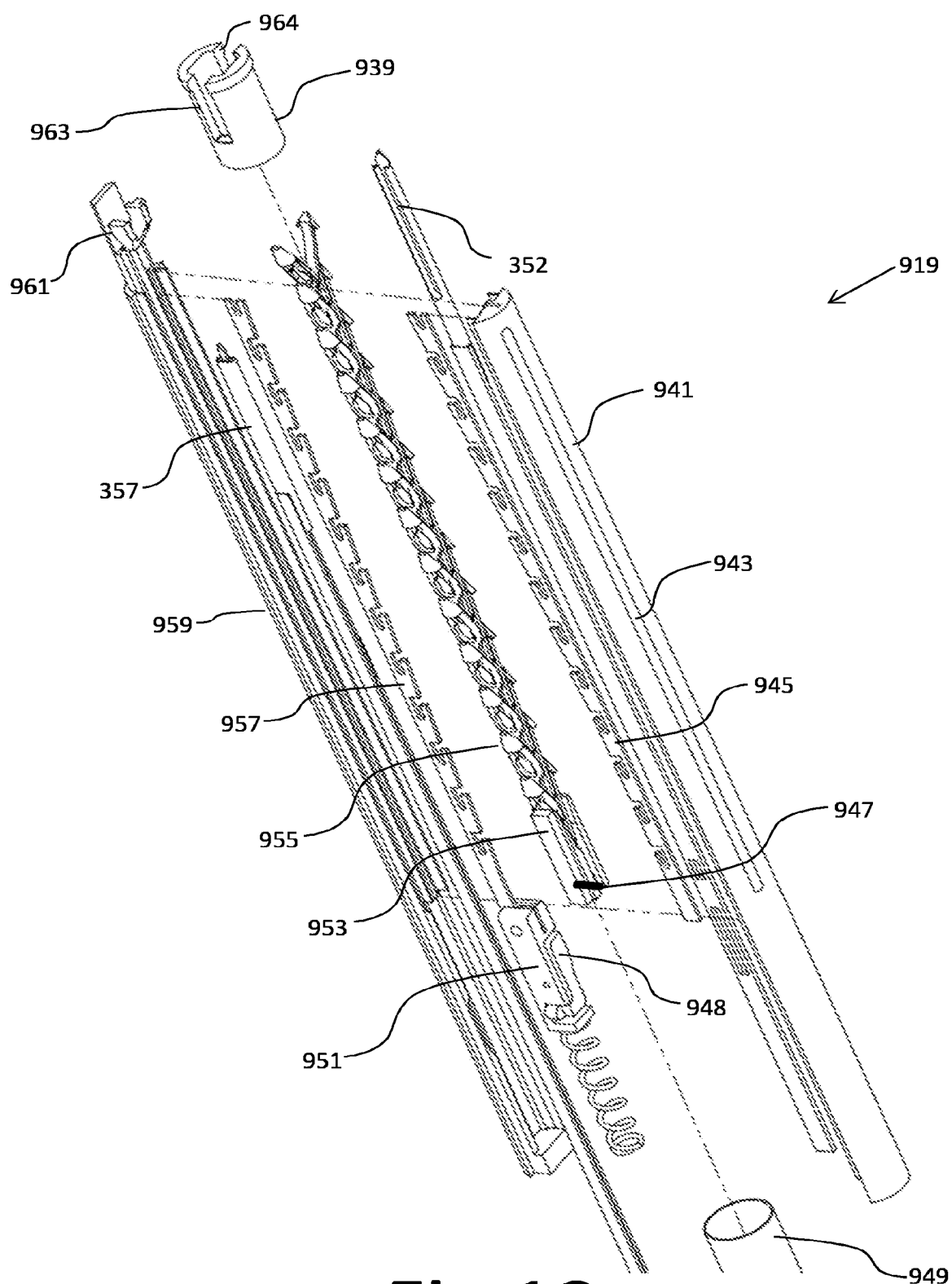
FIG. 19 shows the structure of the clip feeder mechanism.

FIG. 19 shows the structure of the clip feeder 919. FIG. 17 shows hook insertion needle 352 lies under front feeder cover 941, which includes marker slot 943. Front cover 941 covers hold comb 945. Clip stack 955 includes a plurality of suture 250 extending from clip support slide 953, which also includes marker pin 947. Front cover 941 and back cover 959 covering and holding the clip stack 955 and the clip support 953, said front and back cover are encapsulated within the shaft cover 949 and terminate at shaft cap 939. Comb driver assembly 951 with comb driver hook 948 operates drive comb 957, as described below. Clip feeder 919 includes loop insertion needle 357 disposed near clip spreader 961. Shaft cap 939 includes a loop collection slot 963 and a hook collection slot 964. Clip feeder 919 functions to deliver one suture 250 from clip stack 955 per operation of device 100.

Figure 20:
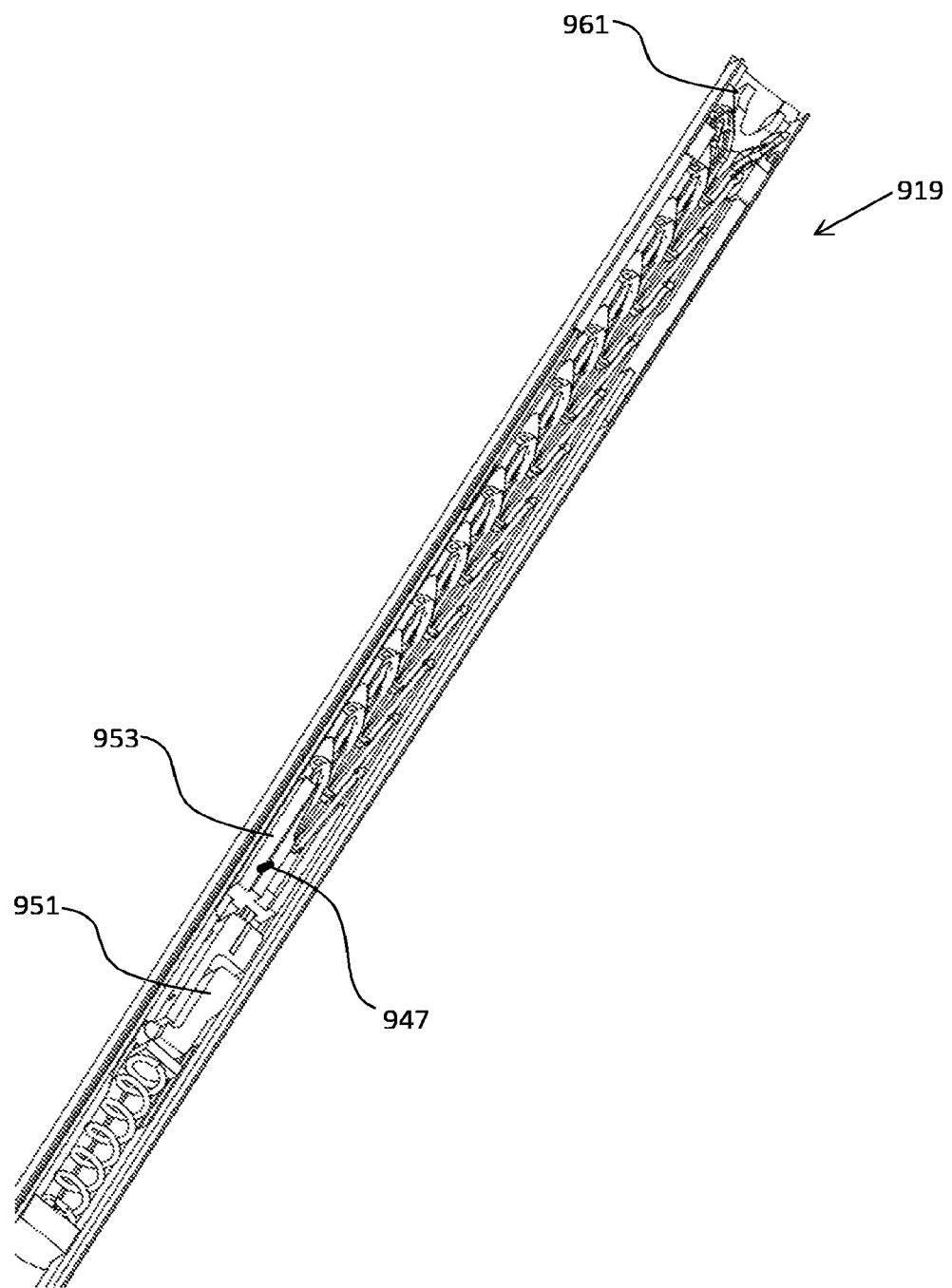
FIG. 20 illustrates the function of the clip feeder.

FIG. 20 illustrates an assembled clip feeder 919. In operation, the comb driver assembly 951 first generates a single up and down stroke of the back drive comb at the end of each application cycle. As a response to the stroke, the entire clip stack 955 is pushed forward by the drive comb 957. During this process the hold comb 945 (not shown) prevents a downward movement of the sutures 250 in clip stack 955. Once the clips stack 955 is pushed upward (e.g., forward), the last suture 250 is spread by the clip spreader 961 and is positioned at the collection slots 963 and 964, ready to be collected by the insertion needles 352 and 357 during the next application cycle. Each suture 250 supports the next suture 250 and prevents the lateral movement of its middle while it is pushed by drive comb 957. The last suture 250 is supported by the clip support slide 953. Clip support slide 953 is pushed by the drive comb 957 together with the clips. A marker pin 947 may protrudes to the outer surface of the shaft, through the marker slots at the feeder covers 941, to indicate to the surgeon how many clips remains in the device.

Figure 21:
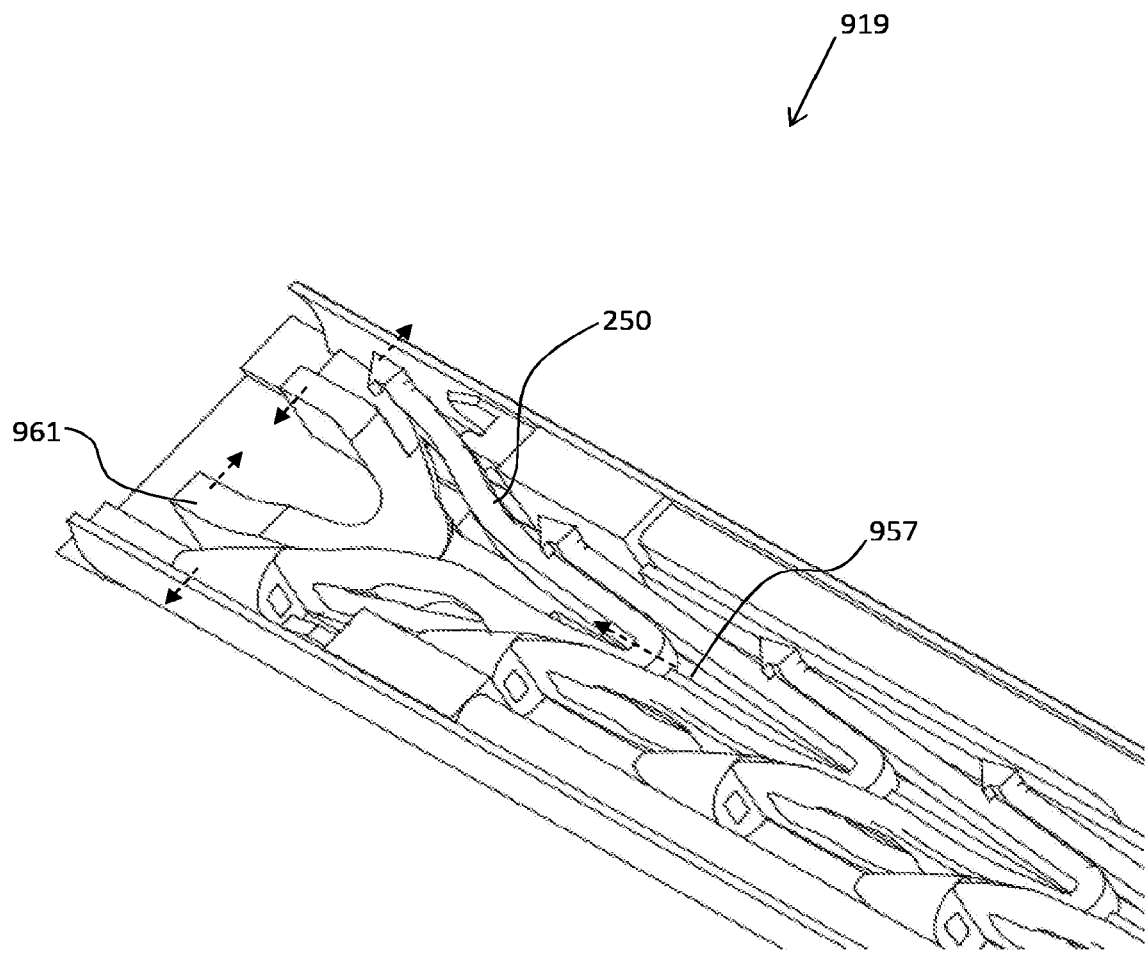
FIG. 21 shows the positioning of a suture in a clip feeder.

FIG. 21 shows the positioning of a suture 250 in clip feeder 919. The arms of spreader 961 are flexible and can flex toward the center of the shaft in order to allow the ends of suture 250 to exit from the device. Spreader 961 also provides resistance in order to allow the integration between needle and the suture 250 and hold the last suture 250 in place before its application. The last suture 250 is pushed forward against the spreader 961 by the drive comb 957. As a result, the ends of suture 250 are spread into the collection slots 963 and 964 from which they are collected by the insertion needles during the insertion process. The bottom side of the spreader 961 in sloped in order to allow the extraction of suture 250 once it was collected by the insertion needles.

Figure 22A:
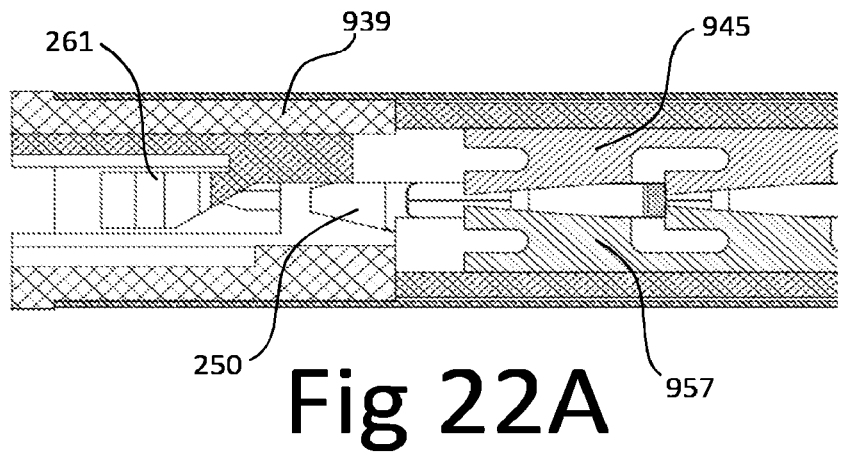
FIGS. 22A-22E show the advancement of a suture through the clip feeder.
Figure 22B:
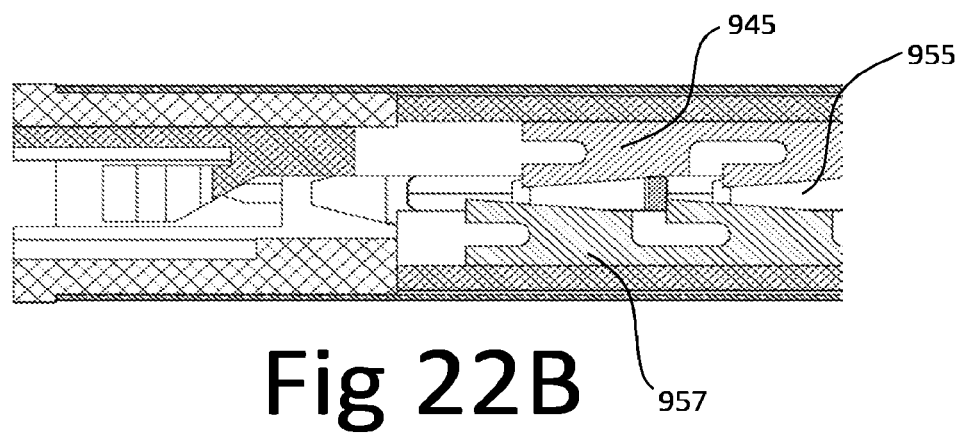
Figure 22C:
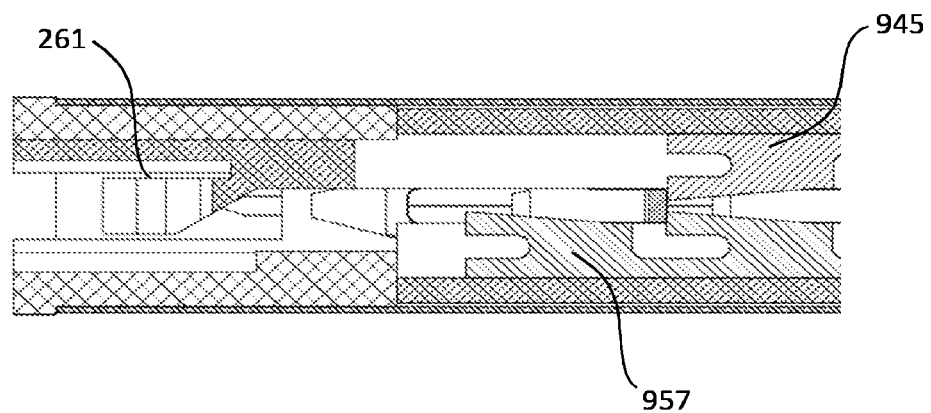

FIGS. 22A-22E show the advancement of a suture 250 through clip feeder 919. FIGS. 22A-22E are cross-sections of a distal end of clip feeder 919 and they depict a loading of a new suture 250 into the collection slots 963 and 964 once a clip suture 250 is applied. FIG. 22A shows shaft cover 939 with clip spreader 961 therein. Also visible is suture 250, being controlled by drive comb 957 and hold comb 945. In an initial stage in FIG. 22A, after the first suture 250 is collected and inserted into the tissue, the next suture 250 is placed below the collection slots 963 and 964. As shown in FIG. 22B, drive comb 957 is moving back while the hold comb 945 is holding the clips stack 955 in place. The teeth of the drive comb 957 are bent while they are climbing over the clip stack 955. FIG. 22C shows drive comb 957 engaged with bottom section of the sutures in clip stack 955.

Figure 22D:
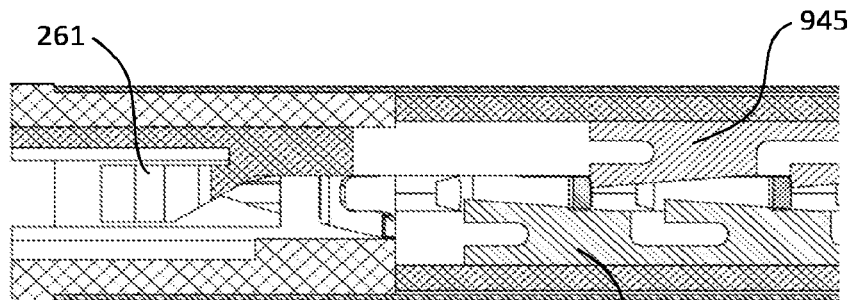
Figure 22E:
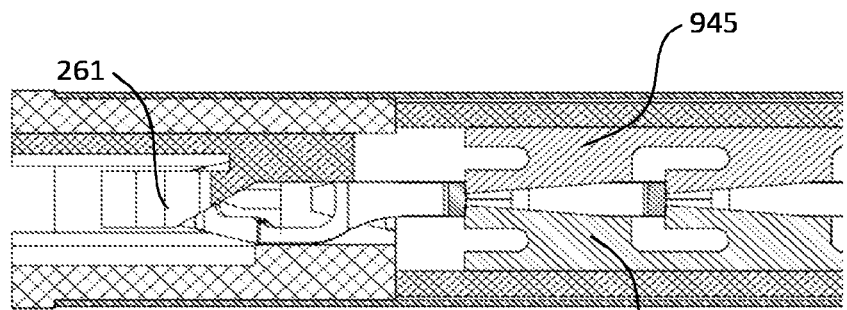

FIG. 22D shows drive comb 957 pushing one of sutures 250 forward and toward the spreader 961 while climbing over the teeth of the hold comb 945 (which are bent during the process). As seen in FIG. 22E, the next suture 250 is positioned at the collection slots 963 and 964 and is ready to be collected by the insertion needles 352 and 357.

Figure 23A:
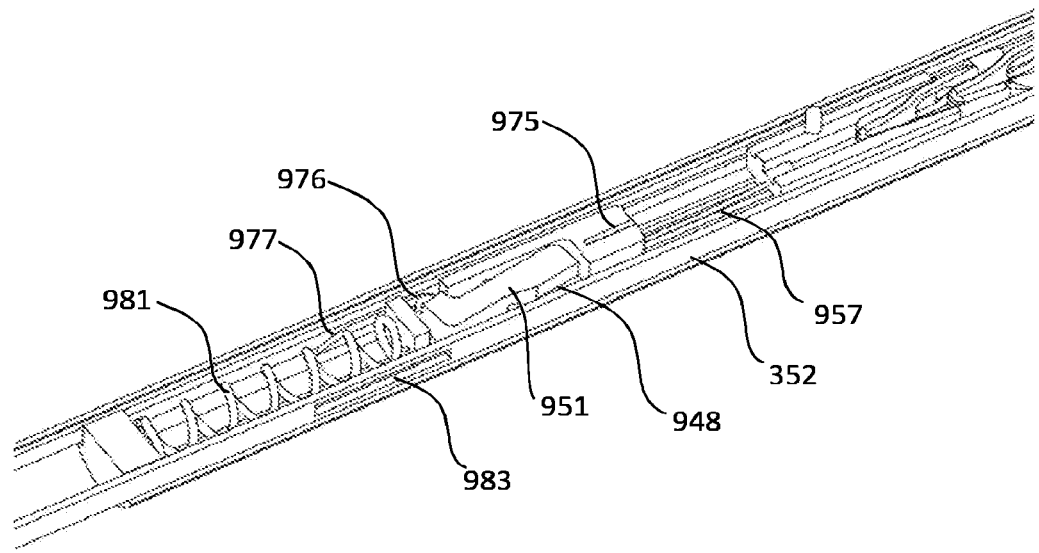
FIGS. 23A-23E depict the operation of the comb driver mechanism of a clip feeder.
Figure 23B:
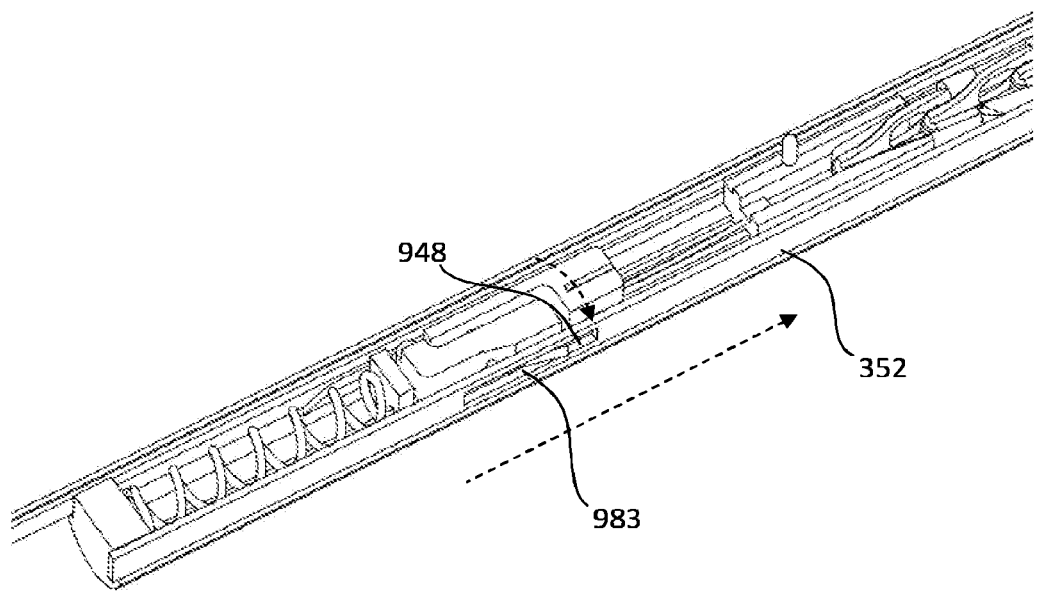

FIGS. 23A-23E depict the operation of the comb driver mechanism of clip feeder 919. As seen in FIG. 23A, comb driver assembly 951 provides a connection between comb driver hook 948 plus comb driver slide 975 and drive comb 957. Release slope 977 and release bulge 976 cooperate to release the comb driver hook from the hook insertion needle. Comb driver spring 981 can be seen by hook slot 983. The comb driver hook 948 is connected to the comb driver slide 975 by a flexible pin, allowing its rotation. FIG. 21A shows an initial stage, in which hook inserting needle 352 is positioned backward. Hook engagement is depicted in FIG. 21B. Once an application cycle starts, hook insertion needle 352 is moved forward. Once the hook slot 983 is positioned in front of the comb driver hook 948, the comb driver hook 948 springs into hook slot 983.

Figure 23C:
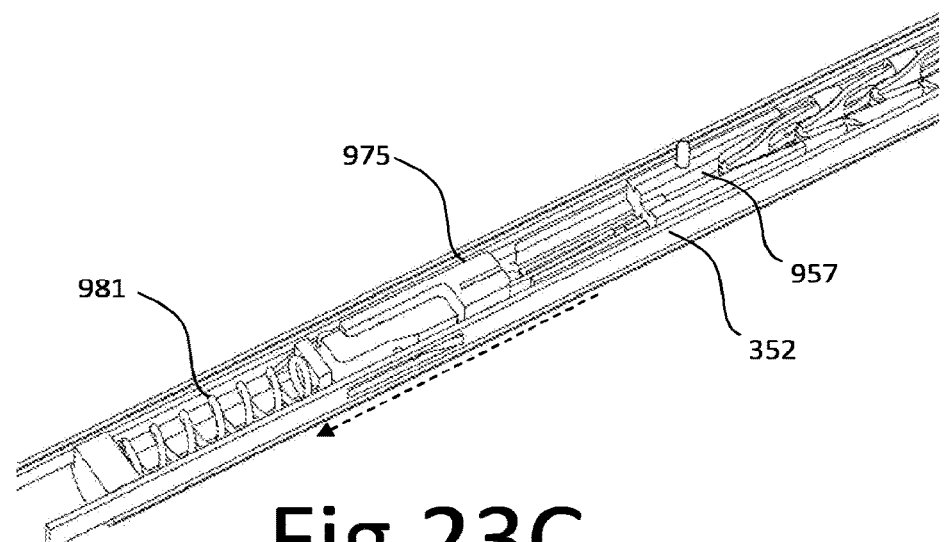
Figure 23D:
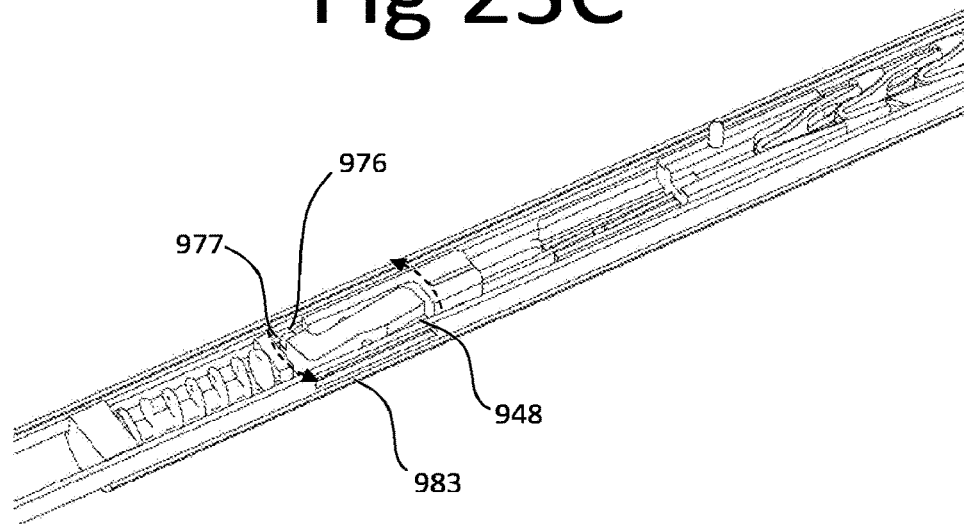
Figure 23E:
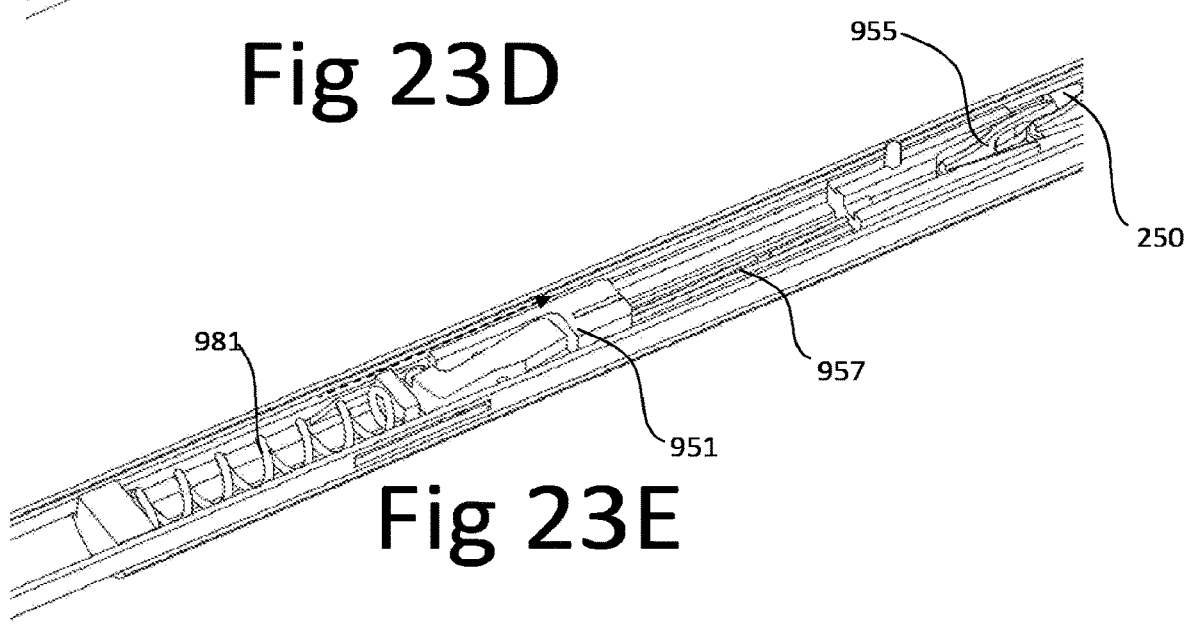

FIG. 23C depicts a pulling back stage. At the final stage of the application cycle, the hook insertion needle 352 moves back while pulling the back the comb driver slide 975 and the drive comb 957 while pressing the comb driver spring 981. During this movement the comb teeth are engaged with sutures 250. FIG. 23D shows release. Once the release bulge 976 reaches the release slope 977, release bulge 976 is pushed laterally and removes the hook 948 out of the hook slot 983. FIG. 23E shows advancement of suture 250. The compressed spring 981 pushes the comb driver 951 and the drive comb 957 forward while advancing the entire clip stack 955.

Figure 24:
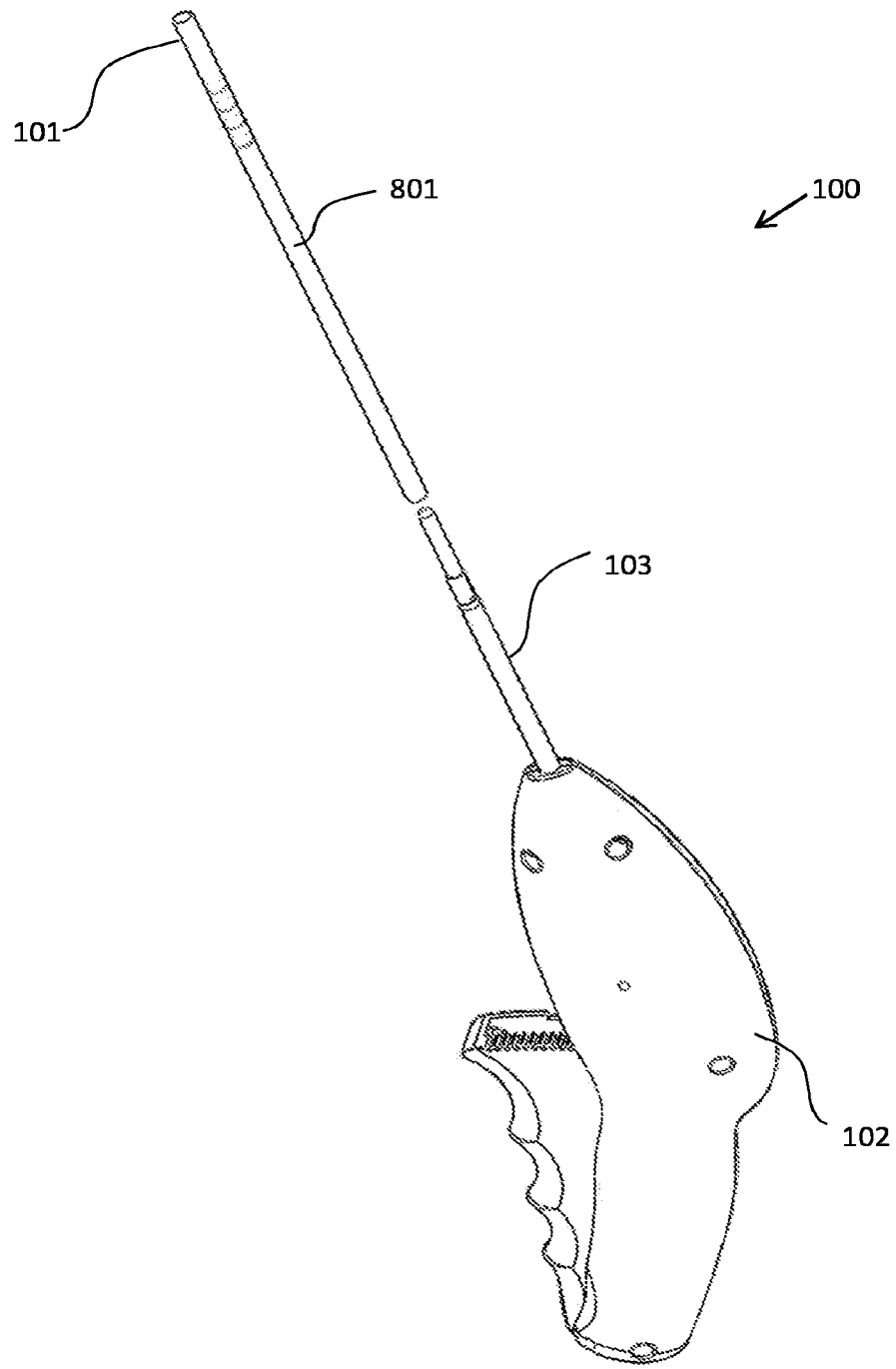
FIG. 24 shows a mechanism for connecting a cartridge.

FIG. 24 depicts a cartridge 801 that can be the entire distal section 101 of the device 100 and hold the feeder mechanism according to certain embodiments of the invention. Any suitable mechanism for loading sutures may be used. For example, as discussed above, sutures can be provided in a cartridge 801 that is loaded into the shaft 103. FIG. 24 depicts an alternative mechanism in which the cartridge 801 is inserted over a hub portion along shaft 103. As shown in FIG. 24, a cartridge can be provided that is configured to be connected to the handle section 102 by a hub section. The hub section can hold the cartridge 801 connected to the handle 102 and deliver the movement from the handle mechanism to the push rods. The locking and releasing of the cartridge to the hub can be obtained by rotating the cartridge inside the hub.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A suturing device comprising:
a trigger on a handle;
an elongated shaft dimensioned for insertion through a surgical incision and extending from the handle;
a plurality of self-locking sutures disposed at least partially within the shaft;
a first needle member disposed at a distal end of a first push rod extending along the shaft; and
a second needle member comprising a flexible, pre-shaped portion and disposed at a distal end of a second push rod extending along the shaft,
wherein when the trigger is squeezed
the first needle member extends from a distal tip of the shaft along a straight path parallel to a longitudinal axis of the shaft to deliver a first end of a first of the plurality of self-locking sutures through a tissue, and
the second needle member extends from the distal tip of the shaft along a curved path to deliver a second end of the first suture through the tissue and connect the second end to the first end, thereby fastening the first suture beneath a surface of the tissue, and further wherein operation of the trigger causes a second of the plurality of sutures to advance towards the distal tip of the shaft upon delivery of the first suture.

2. The suturing device of claim 1, wherein one of the first end and the second end comprises a hook and the other comprises a loop.

3. The suturing device of claim 2, wherein a portion of the first push rod and a portion of the second push rod extend within the shaft and are parallel to the longitudinal axis.

4. The suturing device of claim 3, wherein the shaft is substantially cylindrical.

5. The device of claim 4, wherein the shaft is dimensioned for insertion through a trocar.

6. The device of claim 5, wherein the shaft comprises an articulation joint.

7. The device of claim 6, wherein the articulation joint comprises at least one living hinge to limit a radius of curvature of the joint.

8. The device of claim 3, wherein when the trigger is squeezed the first needle member and the second needle member engage the first end and the second end within the shaft and release the first end and the second end beneath the surface of the tissue.

9. The device of claim 8, wherein the device is configured to insert the first suture to a depth greater than a diameter of the shaft.

10. The device of claim 9, wherein the device is adapted to insert the first suture through a prosthetic mesh.

11. The device of claim 3, further comprising a clip feeder.

12. The device of claim 11, further comprising a cartridge loaded with the plurality of self-locking sutures and disposed at least partially within the shaft.

13. The device of claim 12, wherein the cartridge comprises a distal portion of the shaft.

14. The device of claim 13, wherein the device is configured to receive a cartridge from a set of cartridges, at least two carrying sutures of different sizes.

15. The device of claim 14, wherein the device is configured to deliver sutures of different sizes to different penetration depths.

16. The device of claim 3, further comprising an indicator that shows a number of sutures disposed at least partially within the shaft.

17. The device of claim 16, wherein the indicator is visible on the shaft.

18. A method of fastening a suture to a tissue, the method comprising:
 providing a device comprising:
  a trigger on a handle;
  an elongated shaft dimensioned for insertion through a surgical incision and extending from the handle;
  a plurality of self-locking sutures disposed at least partially within the shaft;
  a first needle member disposed at a distal end of a first push rod extending along the shaft; and
  a second needle member comprising a flexible, pre-shaped portion and disposed at a distal end of a second push rod extending along the shaft,
 wherein when the trigger is squeezed
  the first needle member extends from a distal tip of the shaft along a straight path parallel to a longitudinal axis of the shaft to deliver a first end of a first of the plurality of self-locking sutures through a tissue, and
  the second needle member extends from the distal tip of the shaft along a curved path to deliver a second end of the first suture through the tissue and connect the second end to the first end, thereby fastening the first suture beneath a surface of the tissue, and further wherein operation of the trigger causes a second of the plurality of sutures to advance towards the distal tip of the shaft upon delivery of the first suture;
 contacting the distal tip of the shaft with the tissue; and
 squeezing the trigger, thereby fastening the suture to the tissue.

19. The method of claim 18, further comprising inserting a distal portion of the shaft through a trocar.

\* \* \* \* \*